(12) United States Patent
Lindsey et al.

(10) Patent No.: US 7,718,794 B2
(45) Date of Patent: May 18, 2010

(54) SYNTHESIS OF PORPHYRINS DESIGNED FOR ATTACHMENT TO ELECTROACTIVE SURFACES VIA ONE OR MORE CARBON TETHERS

(75) Inventors: Jonathan S. Lindsey, Raleigh, NC (US);
Robert S. Loewe, Highlands Ranch, CO (US)

(73) Assignees: North Carolina State University, Raleigh, NC (US); ZettaCore, Inc., Englewood, CO (US)

( * ) Notice: Subject to any disclaimer, the term of this patent is extended or adjusted under 35 U.S.C. 154(b) by 8 days.

(21) Appl. No.: 12/052,084

(22) Filed: Mar. 20, 2008

(65) Prior Publication Data
US 2008/0194839 A1 Aug. 14, 2008

Related U.S. Application Data

(62) Division of application No. 10/886,816, filed on Jul. 8, 2004, now Pat. No. 7,378,520.

(51) Int. Cl.
*C07B 47/00* (2006.01)
*C07D 487/22* (2006.01)
*C07D 207/33* (2006.01)

(52) U.S. Cl. ..................... 540/145; 548/518
(58) Field of Classification Search ............. 540/145; 548/518
See application file for complete search history.

(56) References Cited

U.S. PATENT DOCUMENTS

| | | | |
|---|---|---|---|
| 5,955,603 A | 9/1999 | Therien et al. | |
| 5,986,090 A | 11/1999 | Therien et al. | |
| 6,100,392 A | 8/2000 | Therien et al. | |
| 6,212,093 B1 | 4/2001 | Lindsey | |
| 6,272,038 B1 | 8/2001 | Clausen et al. | |
| 6,324,091 B1 | 11/2001 | Gryko et al. | |
| 6,381,169 B1 | 4/2002 | Bocian et al. | |
| 6,407,330 B1 | 6/2002 | Lindsey et al. | |
| 6,420,648 B1 | 7/2002 | Lindsey | |
| 6,451,942 B1 | 9/2002 | Li et al. | |
| 6,559,374 B2 | 5/2003 | Lindsey et al. | |
| 6,596,935 B2 | 7/2003 | Lindsey et al. | |
| 6,603,070 B2 | 8/2003 | Lindsey et al. | |
| 6,642,376 B2 | 11/2003 | Lindsey et al. | |
| 6,657,884 B2 | 12/2003 | Bocian et al. | |
| 6,674,121 B2 | 1/2004 | Misra et al. | |
| 6,728,129 B2 | 4/2004 | Lindsey et al. | |
| 2002/0137925 A1 | 9/2002 | Lindsey et al. | |
| 2002/0180446 A1 | 12/2002 | Kuhr et al. | |
| 2003/0075216 A1 | 4/2003 | Loewe et al. | |
| 2003/0081463 A1 | 5/2003 | Bocian et al. | |
| 2003/0092896 A1 | 5/2003 | Lindsey et al. | |
| 2003/0096978 A1 | 5/2003 | Lindsey et al. | |
| 2003/0096989 A1 | 5/2003 | Lindsey et al. | |
| 2004/0120180 A1 | 6/2004 | Rotenberg et al. | |

FOREIGN PATENT DOCUMENTS

DE 4343268 A1 6/1995

OTHER PUBLICATIONS

Kulyk et al., caplus an 1995:1004637.*
Smeets et al, "A Novel Way of Preparing Meso-Substituted Ethynylporphyrins and Their Derivatives by Using 1,2,3-Thiadiazole as a Protecting Group", 1998, pp. 9841-9844.
DiMagno et al, "Catalytic Conversion of Simple Haloporphyrins Into Alkyl-, Aryl-, Pyridyl-, and Vinyl-Substituted Porphyrins" 1993, pp. 2513-2515.
Sumi et al, "Synthesis of Homopolymer and Water-Soluble Polymers Containing Tetraphenylporphinatomanganese (III) Complex, and Ligand Substitution Reaction for Anionic Ligand", 1994, pp. 1243-1254.
Rao et al, "Rational Syntheses of Porphyrins Bearing up to Four Different Meso Substituents", 2000, pp. 7323-7344.
Mikami et al. "Synthesis and properties of oligo-para-phenylene substituted Porphyrins." *Chemistry Letters* (1997), 8, pp. 833-834.
Simkhovich et al. "Easy Preparation of Cobalt Corrle and Hexaphyrin and Isolation of New Oligopyrroles in the Solvent-free Condensation of Pyrrole with Pentaflurobenzaldehyde." *Organic Letters* (2003), 5(8), pp. 1241-1244.
Notification of the Transmittal of the International Search Report for corresponding International Application No. PCT/US05/18858. Mailed Oct. 13, 2005.
Mikami S. et al. Synthesis and properties of oligo-*para*-phenylene substituted porphyrins. Chemistry Letters (1997), pp. 833-834.
Pomogailo A.D. et al. Synthesis and structure of vinylporphyrin metal complexes and their copolymerization. Spectral luminescence properties of Zn copolymers in solution. Journal of Porphyrins and Phthalocyanines (2000) 4(1): 45-65.

(Continued)

*Primary Examiner*—Kamal A Saeed
*Assistant Examiner*—Michael Barker
(74) *Attorney, Agent, or Firm*—Myers Bigel Sibley & Sajovec, P.A.

(57) ABSTRACT

Porphyrin compounds having a surface attachment group coupled thereto at the 5 position are described. The surface attachment group has the formula:

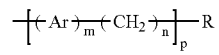

wherein R is —CHCH$_2$ or —CCH and Ar is an aromatic group. Methods and intermediates useful for making such compounds are also described.

13 Claims, 1 Drawing Sheet

OTHER PUBLICATIONS

IUPAC-IUB Joint Commission on Biochemical Nomenclature. Moss GP, ed. Nomenclature of Tetrapyrroles (Recommendations 1986). Pure & Appl. Chem. 1987; 59(6): 779-832. (pp. 779 and 814 submitted).

* cited by examiner

SYNTHESIS OF PORPHYRINS DESIGNED FOR ATTACHMENT TO ELECTROACTIVE SURFACES VIA ONE OR MORE CARBON TETHERS

RELATED APPLICATIONS

This application claims priority to and is a divisional of U.S. patent application Ser. No. 10/886,816, filed Jul. 8, 2004, now U.S. Pat. No. 7,378,520, the disclosure of which is incorporated by reference herein in its entirety.

This application is also related to U.S. patent application Ser. Nos.:

Ser. No. 10/628,868, filed Jul. 28, 2003, titled *Attachment of Organic Molecules to Group III, IV, or V Substrates;*

Ser. No. 10/742,596, filed Dec. 19, 2003;

Ser. No. 10/641,412, filed Aug. 15, 2003, titled *Scalable Synthesis of Dipyrromethanes;*

Ser. No. 10/164,181, filed Sep. 3, 2003, titled *Facile Synthesis of 1,9-diacyldiprromethanes;*

Ser. No. 10/698,255, filed Oct. 31, 2003, titled *Synthesis of Phosphono-substituted Porphyrin Compounds for Attachment to Metal Oxide Surfaces;* and Ser. No. 10/867,512, filed Jun. 14, 2004, titled *A New Route to Formyl-Porphyrins;* the disclosures of which are incorporated by reference herein in their entirety.

GOVERNMENT FUNDING

This invention was made with Government support under Grant No. MDA972-01-C-0072 from the DARPA Moletronics Program. The Government has certain rights to this invention.

FIELD OF THE INVENTION

This invention concerns methods and intermediates for the synthesis of porphyrins, particularly porphyrins suited to attachment to electroactive surfaces.

BACKGROUND OF THE INVENTION

The field of molecular electronics has been driven in part by the prospect that devices that rely on the bulk properties of semiconductors will fail to retain the required characteristics to function when feature sizes reach nanoscale dimensions. As a consequence, there has been much interest in developing molecular-based electronic materials for use in both memory architectures and circuit elements.[1] Towards this goal, we have been engaged in a program aimed at constructing devices that use the properties of molecules to store information.[2-6] In these approaches, a collection of redox-active porphyrinic molecules attached to an electroactive surface serves as the active storage medium, and information is stored in the discrete redox states of the molecules. The focus of this work has been developing a hybrid architecture, where the molecular material is attached to a semiconductor platform. The implementation of hybrid molecular/semiconductor architectures as a transition technology leverages the vast infrastructure of the semiconductor industry with the advantages afforded by molecular-based active media.

The success of such a hybrid architecture requires, in general, (1) a straightforward means of attaching porphyrins to an electroactive surface, particularly large-wafer silicon, and (2) a robust linkage that can withstand large numbers of redox cycles. A number of methods have been developed for covalent attachment of organic molecules to silicon surfaces.[7] For example, the reaction of Si (hydrogen-passivated or chlorine-modified) with an alcohol affords the self-assembled film containing RO—Si linkages. However, the reaction requires use of neat liquids or a very high concentration of the molecules to be attached.[8-11] Porphyrins generally have low solubility in organic solutions, with concentrations of ~50 mM being a typical upper limit. The method we previously developed for attaching porphyrins to Si platforms (either hydrogen-passivated or iodine-modified) involved depositing a drop of solution containing the porphyrin compound in a high-boiling solvent (e.g., benzonitrile, bp 191° C.) onto a photolithographically patterned micron-size Si electrode, followed by heating at ~170° C. for several hours, during which time additional solvent was added to the sample area.[6] This method afforded attachment of porphyrins[6] (and ferrocenes[3,6]) to Si(100) via tethers that are terminated with OH, SAc, and SeAc groups, yielding RO—Si, RS—Si, and RSe—Si linkages (the acetyl protecting group is cleaved upon attachment) where R represents the tether and accompanying redox-active unit.[12] This procedure produced high quality monolayers useful for academic studies but was unsuited for reproducible fabrication of memory chips on large Si wafers. In addition, in the past few years it has become apparent that more stable monolayers are generally obtained with carbosilane linkages (RC—Si) than alkoxysilane linkages (RO—Si). Achieving a stable linkage of the redox-active unit to the Si surface is essential because as many as $10^{15}$ cycles may be encountered over an operational lifetime in a memory chip.[13]

A number of methods have been developed for derivatizing silicon surfaces via carbosilane linkages.[7] The methods include pyrolysis of diacyl peroxides,[14,15] reaction of Grignard reagents (with halogenated silicon surfaces),[16] and electrografting of aryldiazonium salts,[17] alkyl halides,[18] or Grignard reagents.[19] Alkenes have been employed for attachment to Si via thermal,[15,20,21] free radical,[15] photochemical (UV),[22-24] and Lewis-acid mediated reactions.[25,26] Alkynes have been less studied but generally appear to react via the same methods as for alkenes, including thermal,[27] free radical,[15] photochemical,[28] Lewis-acid mediated,[26,28] and electrografting processes.[28]

SUMMARY OF THE INVENTION

The thermal attachment methods (typically ~100° C.) with alkenes or alkynes are attractive for attaching porphyrinic compounds to large-scale Si wafers. However, the requirement for use of very high concentrations of reactants appeared to exclude such an application. The present invention provides for, among other things, the convenient synthesis of such compounds in useful forms.

A first aspect of the present invention is a porphyrin compound having a surface attachment group coupled thereto at the 5 position, said surface attachment group having the formula:

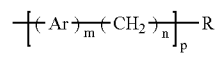

wherein:
R is —CHCH$_2$ or —CCH;
Ar is an aromatic group;
m is 0 to 4;
n is 0 to 6; and
p is 0 or 1 to 3;

said porphyrin compound preferably subject to the proviso that n is at least 1 or m is at least 2, and p is at least 1.

A second aspect of the present invention is a method of making a porphyrin compound having a surface attachment group coupled thereto at the 5 position, said surface attachment group having the formula:

wherein R, Ar, m, n and p are as described above, the method comprising: (a) reacting a dipyrromethane with a dipyrromethane-1,9-dicarbinol to produce a reaction product; and then (b) oxidizing said reaction product to produce said porphyrin compound, wherein either or both of said dipyrromethane and said dipyrromethane-1,9-dicarbinol is substituted with said surface attachment group at the 5 position.

A further aspect of the invention is a method of making a porphyrin compound having a vinyl surface attachment group coupled thereto at the 5 position, said method comprising: (a) halogenating a porphyrin at the 5 position to produce an intermediate; and then (b) reacting said intermediate with a vinyl stannane in the presence of a palladium (0) catalyst in a Stille cross-coupling reaction to produce said porphyrin compound having a vinyl surface attachment group coupled thereto at the 5 position.

A further aspect of the invention is a dipyrromethane compound having a surface attachment group coupled thereto at the 5 position, said surface attachment group having the formula:

wherein R, Ar, m, n and p are as described above, said dipyrromethane compound preferably subject to the proviso that n is at least 1 or m is at least 2, and p is at least 1. In some embodiments the dipyrromethane is a 1,9-diacyldipyrromethane.

A further aspect of the invention is a method of making a dipyrromethane compound having a surface attachment group coupled thereto at the 5 position, said surface attachment group having the formula:

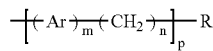

wherein R, Ar, m, n and p are as described above; said method comprising: reacting a precursor compound of the formula:

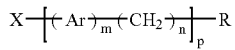

where X is an aldehyde or acetal group, with a pyrrole to produce said dipyrromethane compound having said surface attachment group substituted therein at the 5 position.

A further aspect of the present invention is a method of making a 1,9-diacyldipyrromethane metal complex, comprising: (a) acylating a dipyrromethane compound having a surface attachment group coupled thereto at the 5 position, said surface attachment group having the formula:

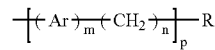

wherein R, Ar, m, n and p are as described above, to form a mixed reaction product comprising a 1,9-diacyldipyrromethane; (b) combining said mixed reaction product with a compound of the formula $R'_2MX_2$ in the presence of a base, where R' is alkyl or aryl, M is Sn, Si, Ge, or Pb, and X is halo, OAc, acac or OTf, to form a metal complex of the formula $DMR'_2$ in said mixed reaction product, wherein $DH_2$ is a 1,9-diacyldipyrromethane; and then (c) separating said metal complex from said mixed reaction product.

The present invention is explained in greater detail in the drawings herein and the specification set forth below.

DETAILED DESCRIPTION OF THE PREFERRED EMBODIMENTS

Figure 1:
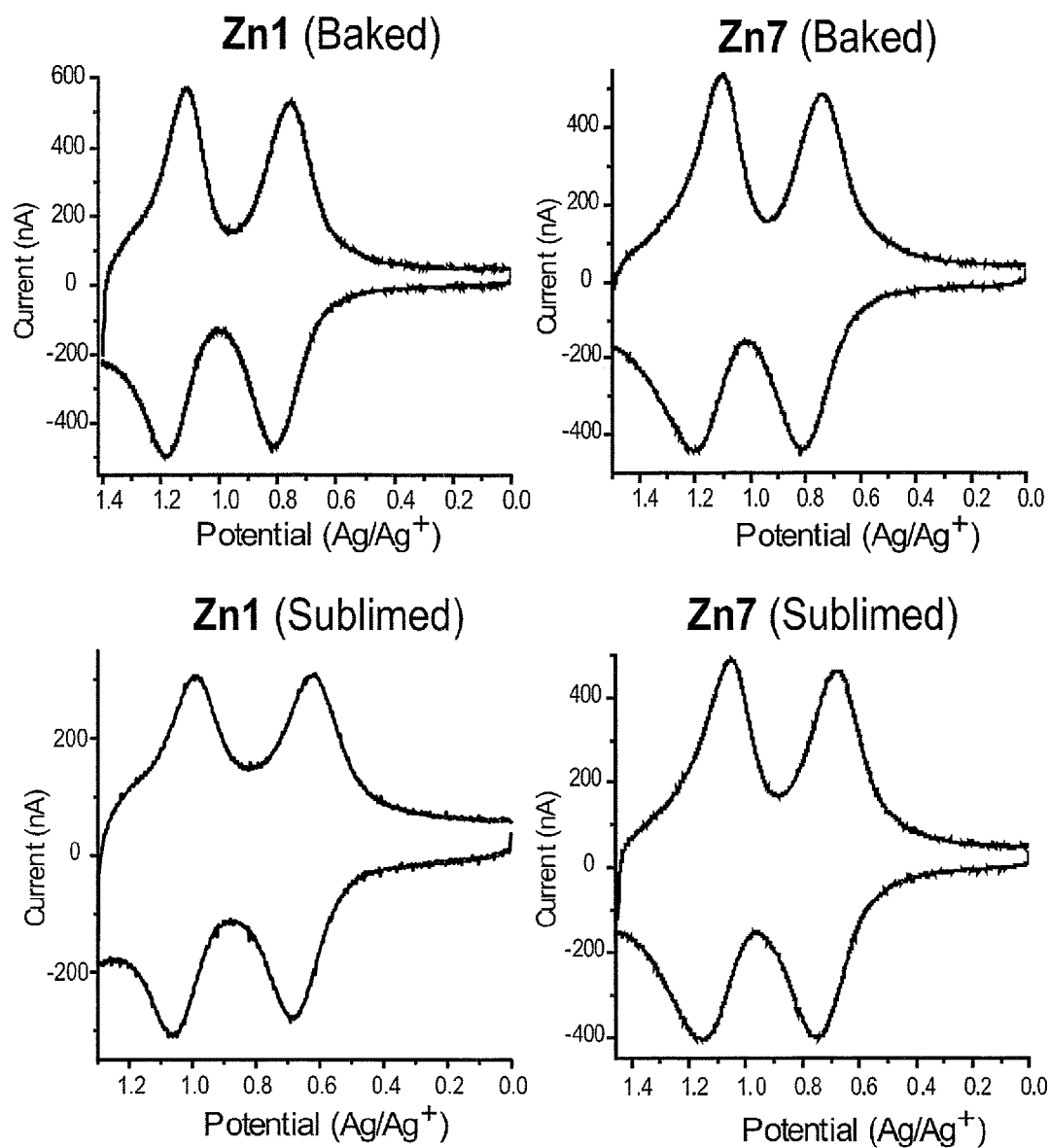
FIG. 1. Fast-scan cyclic voltammograms (100 Vs$^{-1}$) of monolayers of Zn1 and Zn7 on p-type Si(100) microelectrodes. The solvent/electrolyte overlayer is composed of propylene carbonate containing 1.0 M Bu$_4$NPF$_6$.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like, which may be substituted or unsubstituted.

The term "aryl," as used herein, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like, which may in turn be substituted or unsubstituted.

"Halo" as used herein includes fluoro, chloro, bromo, and iodo.

"Dipyrromethane" as used herein includes both unsubstituted and substituted dipyrromethanes, which may be substituted one or more times at the 1, 2, 3, 5, 7, 8 or 9 positions with any suitable substituent such as halo, carbonyl, alkyl, fluoroalkyl including perfluoroalkyl, aryl (e.g., aryl at the 5 position; alkyl at the 1 and/or 9 position), fluoroaryl including perfluoroaryl, etc. Dipyrromethanes may be coupled to porphyrinic macrocycles at any suitable position on the dipyrromethanes, including the 1, 2, 3, 5, 7, 8, or 9 position.

"Aldehyde group" as used herein refers to a group of the formula —C(=O)H or —RC(=O)H, in which a carbonyl group is bonded to one hydrogen atom and to an R group. Any suitable organic R group, or hydrogen as an R group, may be used in the aldehyde, including aliphatic (e.g., alkyl) and aromatic or aryl R groups (all of which may be substituted or unsubstituted), with particular examples including porphyrin, dipyrrin, and diacyldipyrromethane R groups (all of which may be substituted or unsubstituted). Examples of particular aldehydes that may be used include but are not limited to: formaldehyde, paraformaldehyde, acetaldehyde, propionaldehyde, n-butyraldehyde, benzaldehyde, p-nitrobenzaldehyde, p-tolualdehyde, salicylaldehyde, phenylacetaldehyde, α-methylvaleraldehyde, β-methylvaleraldehyde, γ-methylvaleraldehyde, 4-pyridine carboxaldehyde, pentafluorobenzaldehyde, 4-ethynylbenzaldehyde, 4-[2-(triisopropylsilyl)ethynyl]benzaldehyde, 4-[3-methyl-3-hydroxy-but-1-ynyl)benzaldehyde, 4-(S-acetylthiomethyl)benzaldehyde, 4-(Se-acetyl-selenomethyli)benzaldehyde, 4-(hydroxymethyl)benzaldehyde, 4-vinylbenzaldehyde, 4-allylbenzaldehyde, 4-cyanobenzaldehyde, 4-iodobenzaldehyde, 4-(bromomethyl)benzaldehyde, 4-(2-bromoethyl)benzaldehyde, 4-(1,3-dithiolan-2-yl)benzaldehyde, 4-(1,3-dithian-2-yl)benzaldehyde, 4-(4,4,5,5-tetramethyl-1,3,2-dioxaborolan-2-yl) benzaldehyde, 4-(acetoxymethyl)benzaldehyde, 4-[2-(trimethylsilyl)ethoxy-carbonyl]benzaldehyde, 4-methoxycarbonylbenzaldehyde, 5-[4-(di-tert-butyloxyphosphoryl)benzaldehyde, 5-[4-(diethoxyphosphoryl)benzaldehyde, 5-[4-(di-tert-butyloxyphosphorylmethyl)benzaldehyde, 5-[4-(diethoxyphosphorylmethyl)benzaldehyde, 1,1,1-tris[4-(diethoxyphosphorylmethyl)phenyl]-1-(4-formylphenyl)methane, 1,1,1-tris[4-(S-acetylthiomethyl)phenyl]-1-(4-formylphenyl)methane, 3-(S-acetylthiomethyl)benzaldehyde, 3,5-diethynylbenzaldehyde, 3,5-bis[2-(triisopropyl-silyl)ethynyl]benzaldehyde, 4-(5,10,15-tri-p-tolylporphinatozinc(II)-20-yl)benzaldehyde, 4-(5,10,15-tri-p-tolylporphin-20-yl)benzaldehyde, 4-(dipyrrin-5-yl)benzaldehyde, 4-[1,9-bis(4-methylbenzoyl)dipyrromethan-5-yl]benzaldehyde, 4-ferrocenylbenzaldehyde, propargyl aldehyde, bromomethylpropargyl aldehyde, chloromethylpropargyl aldehyde, S-acetylthiomethylpropargyl aldehyde, 4-(hydroxymethyl)phenylpropargyl aldehyde, hydroxyacetaldehyde, and pyruvic aldehyde.

"Acetal group" as used herein refers to compounds known as "latent aldehydes" that produce the same products as can be produced with an aldehyde as described above in reactions of the present invention. Acetal groups are in general compounds of the general formula —RC(—OR')(—OR")H or —C(—OR')(—OR")H, wherein R is as given in connection with aldehydes above and R' and R" are any suitable organic substituent such as alkyl or aryl (e.g., methyl, ethyl, propyl, butyl, phenyl).

"Porphyrin" as used herein refers to a cyclic structure typically composed of four pyrrole rings together with four nitrogen atoms and two replaceable hydrogens for which various metal atoms can readily be substituted. Porphyrins may be substituted or unsubstituted. A typical porphyrin is hemin.

"Bronsted acid" as used herein refers to a molecular entity (and corresponding chemical species) that is a proton donor to a base. Any suitable Bronsted acid may be used as a catalyst, with examples including but not limited to: trifluoroacetic acid, trichloroacetic acid, oxalic acid, taurine, malonic acid, formic acid, acetic acid, and NH$_4$Cl.

"Lewis acid" as used herein refers to a molecular entity (and corresponding chemical species) that is an electron-pair acceptor and therefore able to react with a Lewis base to form a Lewis adduct, by sharing the electron pair furnished by the Lewis base.

Applicants specifically intend the disclosures of all US Patent references cited herein to be incorporated by reference herein in their entirety.

Porphyrin compounds and synthesis thereof. As noted above, the present invention provides porphyrin compounds having a surface attachment group coupled thereto at the 5 position, the surface attachment group having the formula:

wherein:
R is —CHCH$_2$ or —CCH (in some embodiments preferably —CHCH$_2$);
Ar is an aromatic group(in some embodiments preferably a phenyl group);
m is 0, 1, 2, 3 or 4 (in some embodiments preferably at least 2; in other embodiments preferably 0, 1 or 2);
n is 0, 1 or 2 to 3, 4, 5 or 6 (in some embodiments preferably at least 1, e.g., 1 or 2) (in some embodiments m and n together total 1, 2, 3, 4 or 5); and
p is 0, 1, 2 or 3 (in some embodiments preferably 1 or 2);

Such compounds can be produced by the methods and procedures set forth in greater detail below.

A method of making a porphyrin compound having a surface attachment group coupled thereto at the 5 position as described above (which method is exemplified by Scheme 5 below) comprises: (a) reacting (i.e., condensing) a dipyrromethane with a dipyrromethane-1,9-dicarbinol to produce a reaction product; and then (b) oxidizing said reaction product to produce said porphyrin compound, wherein either or both of said dipyrromethane and said dipyrromethane-1,9-dicarbinol is substituted with said surface attachment group at the 5 position. In general, the condensing step is carried out in a polar or nonpolar solvent in the presence of a Lewis acid followed by oxidation with an oxidizing agent such as DDQ in accordance with known techniques. In some embodiments the solvents used to carry out the present invention preferably have a dielectric constant of about 20, 15, or 10 or less, at room temperature (i.e., 25° C.). The solvent may be a single compound or mixtures thereof. Preferably the solvent is nonaqueous. Particular examples of suitable solvents include, but are not limited to, chlorinated aliphatic hydrocarbons (e.g., dichloromethane, chloroform, 1,2-dichloroethane, 1,1,1-trichloroethane, 1,1,2,2-tetrachloroethane, 1,1-dichloroethylene, cis-1,2-dichloroethylene, trans-1,2-dichloroethylene, trichloroethylene, etc.); chlorinated aromatic hydrocarbons (e.g., chlorobenzene, 1,2-dichlorobenzene, 1,3-dichlorobenzene, 1,4-dichlorobenzene, 1-chloronaphthalene, etc.); hydrocarbons (e.g., benzene, toluene, xylene, ethylbenzene, mesitylene, durene, naphthalene); ethers (e.g., ethyl ether, propyl ether, tetrahydrofuran, p-dioxane, anisole, phenyl ether, etc.); esters (e.g., ethyl acetate, methyl acetate, ethyl benzoate, butyl phthalate, etc.); glymes (e.g., 2-methoxyethanol, 2-butoxyethanol), and other solvents such as carbon disulfide, tributyl borate, etc., and mixtures of the foregoing. Note that some solvents may be less preferred: for example, an oxygen in diethyl ether may coordinate with and tie up the Lewis acid, and hence be less preferred. Any suitable electron-pair acceptor may be used as the Lewis acid catalyst in the present invention, including, but not limited to, CsCl, SmCl$_3$.6H$_2$O, InCl$_3$, CrF$_3$, AlF$_3$, Sc(OTf)$_3$, TiF$_4$, BEt$_3$, GeL$_4$, EuCl$_3$.nH$_2$O, LaCl$_3$, Ln(OTf)$_3$ where Ln=a lanthanide, etc. The concentration may range, for example, from 0.001 or 0.01 mmol/L to 100 or 500 mmol/L, or more. Specific examples of Lewis acids and suitable concentrations thereof include InC$_3$ (0.32 mmol/L), Sc(OTf)$_3$ (0.32 mmol/L), Yb(OTf)$_3$ (1.0 mmol/L), and Dy(OTf)$_3$ (0.32 mmol/L). See, e.g., Lindsey et al., U.S. patent application Ser. No. 2003/0096978 (May 22, 2003). The reaction conditions of the present invention are not critical. In general, the reactions may be carried out at any suitable temperature and pressure, such as room temperature and ambient pressure. In general the reactions are rapid (e.g., are carried out for a time of from 1 to 10 minutes), and preferably are carried out within a time of 1 to 2 hours. The dipyrromethane-1,9-dicarbinol can be produced by reducing a 1,9-diacyldipyrromethane to form the dipyrromethane 1-9-dicarbinol, in accordance with known techniques.

Vinyl porphyrin compounds and synthesis thereof. A further aspect of the invention is a method (an example of which is illustrated in Scheme 6 below) of making a porphyrin compound having a vinyl surface attachment group coupled thereto at the 5 position, said method comprising: (a) halogenating a porphyrin at the 5 position to produce an intermediate; and then (b) reacting said intermediate with a vinyl stannane in the presence of a palladium (0) catalyst in a Stille cross-coupling reaction to produce said porphyrin compound having a vinyl surface attachment group coupled thereto at the 5 position. The Stille reaction is known and can be carried out in accordance with known techniques, such as those described in U.S. Pat. Nos. 6,482,851; 6,380,394, 6,197,922; 6,136,157; and 5,849,922, or variations thereof that will be apparent to those skilled in the art in light of the disclosure provided herein. In general, the Stille reaction may be carried out with a palladium(0) catalyst, typically with a trialkyl or triaryl P or As compound as the ligand(s), and with a vinyl stannane, typically a (vinyl)trialkylstannane, as the other reactant. The reaction conditions are not critical, and the reaction may be conveniently carried out in a non-polar organic solvent such as tetrahydrofuran, toluene, or mixture thereof, at any suitable temperature (e.g., 0 to 150° C.). The porphyrin itself may be conveniently produced by reacting a dipyrromethane with a dipyrromethane-1,9-dicarbinol to produce a reaction product; and then oxidizing the reaction product to produce said porphyrin.

Dipyrromethanes and synthesis thereof. As also noted above, a further aspect of the present invention is a dipyrromethane compound having a surface attachment group coupled thereto at the 5 position, said surface attachment group having the formula:

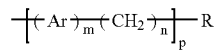

wherein R, Ar, m, n and p are as described above. Such compounds include 1,9-diacyldipyrromethane (as exemplified by Scheme 4 below). Such compounds can be made by reacting a precursor aldehyde or acetal compound of the formula:

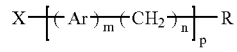

where X is an aldehyde or acetal group and R, Ar, m, n and p are as given above with a pyrrole to produce the desired dipyrromethane compound having the surface attachment group substituted therein at the 5 position. Such methods are exemplified by Scheme 3 below. In general, such methods comprise the step of (a) providing a reaction system comprising, consisting of or consisting essentially of an aldehyde or acetal as described above, excess pyrrole and a catalyst. The amount of the aldehyde or acetal in the reaction system will vary depending upon the particular aldehyde or acetal used, but in general the molar ratio of the pyrrole to the aldehyde or acetal is 50:1 to 5,000:1. Stated differently, in general the amount of aldehyde or acetal is from 0.05 or 0.5 to 1 or 5 percent by weight of the system, or more, and the amount of pyrrole in the system is generally from 95 or 98 to 99 or 99.9 percent by weight of the system, or more. The catalyst may be a Bronsted acid or a Lewis acid, and the amount of catalyst in the system is, in general, from 0.01 or 0.1 to 0.5 or 1 percent by weight of the system, or more. Stated otherwise, the molar amount of acid is generally about 0.01 to 100 times the molar amount of aldehyde or acetal in the system. Preferably the system contains not more than 5 or 10 percent by weight water as noted above, and more preferably the system is non-aqueous. The next step of the method involves (b) reacting the aldehyde or acetal with the pyrrole in the reaction system to form the dipyrromethane therein. The reaction temperature is not critical, but in general may be from −20 or 0 to 100° C., or more, and is preferably room temperature. The pressure of the system during the reaction is not critical, but is conveniently ambient pressure. The reaction may be carried out for any suitable time, typically up to 24 hours, and preferably up to one hour. After the reaction step, the method preferably involves (c) quenching the reaction system by adding a base thereto. The base is preferably added without simultaneously adding an organic solvent or water to the reaction system, and in a preferred embodiment the reaction system hence remains non-aqueous during quenching. In general, at least 1 equivalent of base per acid catalyst, tip to 10 equivalents of base per acid catalyst, is added. The base may conveniently be added as a pure or neat substance (which may be a liquid or dry powder), a slurry in pyrrole, etc. The method then may then involve (d) separating the catalyst from the (preferably non-aqueous) reaction system, preferably by a filtration technique (such as suction filtration or pressure filtration) or a gravity technique (such as centrifugation or settling, e.g., with subsequent decanting); and then (e) separating the pyrrole from the (preferably non-aqueous) reaction system to produce the dipyrromethane as a residual (e.g., by pumping off or evaporating the pyrrole). As noted above, the method may optionally include the further step of (f) crystallizing the resultant dipyrromethane, which crystallization may be carried out in accordance with conventional techniques.

Making 1,9-diacyldipyrromethane metal complexes. A further aspect of the present invention is method of making a 1,9-diacyldipyrromethane metal complex (exemplified by Scheme 4 below). In general such methods comprise: (a) acylating a dipyrromethane compound having a surface attachment group coupled thereto at the 5 position, said surface attachment group having the formula:

wherein R, Ar, m, n and p are as described above, to form a mixed reaction product comprising a 1,9-diacyldipyrromethane; (b) combining said mixed reaction product with a compound of the formula $R_2MX_2$ in the presence of a base, where R is alkyl or aryl, M is Sn, Si, Ge, or Pb, and X is halo, OAc (where OAc is acetate), acac (acetylacetonate) or OTf (where OTf is triflate), to form a metal complex of the formula $DMR_2$ in said mixed reaction product, wherein $DH_2$ is a 1,9-diacyldipyrromethane; and then (c) separating said metal complex from said mixed reaction product. Suitable bases include but are not limited to triethylamine, tributylamine, N,N-diisopropylamine, DBU, DBN, and 2,6-di-tert-butylpyridine. The time and temperature of the combining step is not critical, but may for example be from 1 or 2 minutes to 24 hours in duration, and is most conveniently carried out for 10 minutes to two hours, at a temperature range of –20° C. to 50 or 100° C. or more (e.g., room temperature). Any suitable organic solvent may be used, including but not limited to methylene chloride, chloroform, 1,2-dichloroethane, toluene, chlorobenzene, etc. Where complexation of the diacyldipyrromethane is carried out with a compound of the formula $R_2MX_2$, that compound may be free in the reaction solution or immobilized on a solid support such as a polymer support, where the groups R constitute a portion of the polymer or are otherwise coupled to the polymer (with immobilization on the solid support facilitating the subsequent separation of the acylated dipyrromethane product). The methods described herein may further comprise the step of: (d) treating the metal complex with an acid to produce a 1,9-diacyldipyrromethane. Any suitable acid may be used, including but not limited to trifluoroacetic acid, trichloroacetic acid, acetic acid, HCl, p-toluenesulfonic acid. In other embodiments, the methods described herein may further comprise the steps of: (d) reducing the metal complex with a base such as $NaBH_4$ to form a diol from the 1,9-diacyldipyrromethane; and then (e) condensing the diol with a dipyrromethane to form a porphyrin ring compound therefrom.

Utility. The porphyrin compounds of the invention are useful, among other things, for the production of polymers thereof which may be immobilized or coupled to a substrate and used as light harvesting rods, light harvesting arrays, and solar cells, as described for example in U.S. Pat. No. 6,407,330 to Lindsey et al. or U.S. Pat. No. 6,420,648 to Lindsey. Porphyrinic macrocycles or porphyrin compounds of the invention are also useful immobilized to a substrate for making charge storage molecules and information storage devices containing the same. Such charge storage molecules and information storage devices are known and described in, for example, U.S. Pat. No. 6,208,553 to Gryko et al.; U.S. Pat. No. 6,381,169 to Bocian et al.; and U.S. Pat. No. 6,324,091 to Gryko et al. The porphyrinic macrocycle may comprise a member of a sandwich coordination compound in the information storage molecule, such as described in U.S. Pat. No. 6,212,093 to Li et al. or U.S. Pat. No. 6,451,942 to Li et al.

The present invention is explained in greater detail in the non-limiting Examples set forth below.

EXPERIMENTAL

The success of thermal attachment method with alcohol tethers (both for porphyrins and other types of molecules)[6] combined with the fact that porphyrins are known to be stable at very high temperatures (400° C. under inert atmosphere conditions)[4] where other types of organic molecules decompose prompted us to explore very high temperature processing strategies. Two high-temperature processing conditions that enable attachment to Si(100) of porphyrins containing a wide variety of functional groups were developed. The conditions entail direct deposition of the sample onto the Si substrate or sublimation onto the Si substrate. The porphyrins examined initially were those that bear functional groups known to attach to silicon, such as the benzyl alcohol porphyrin Zn1.[6] It was subsequently found that a number of hydrocarbon tethers also afford attachment. The latter finding prompted the synthesis of a systematic set of porphyrins bearing a wide variety of hydrocarbon tethers.

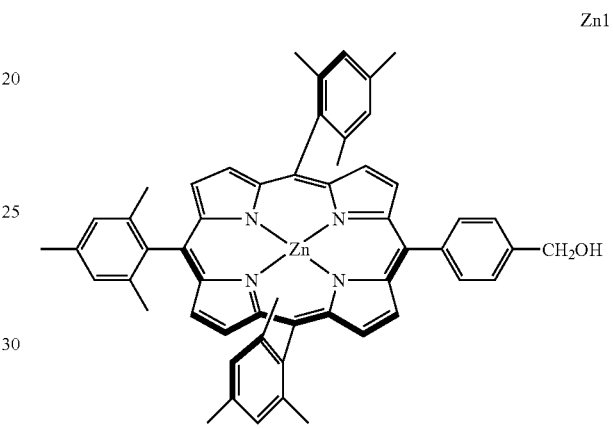

In this application, we first describe the synthesis of the porphyrins bearing hydrocarbon tethers. We then describe the two high-temperature processing methods for attachment to silicon substrates. Taken together, this work greatly expands the scope of porphyrins that can be attached to silicon and enables attachment under conditions suitable for reproducible fabrication.

Results and Discussion

1. Molecular Design. The porphyrins examined herein are designed to probe (1) the effects of the tether (length, composition, terminal functional group) on the ease of attachment and quality of the resulting monolayers on silicon, (2) the ability to attach to silicon via two linkages, and (3) the effects of the size and pattern of nonlinking substituents on the charge-storage properties of the resulting monolayers on silicon. The motivation for these studies stems from the fact that the electron-transfer rates vary depending on the nature of the tether[2,5] and on the surface density[6] of the attached redox-active molecules. Most of the porphyrins are zinc chelates, bear a tether at one meso site, and incorporate inert groups at the three nonlinking meso sites. Within this class, one set of molecules varies the nature of the surface attachment group (iodo, bromomethyl, ethyne, vinyl, allyl; Zn2-Zn7; Chart 1) with mesityl groups at the three nonlinking meso sites. A second set of molecules varies the steric bulk of the nonlinking meso substituents (p-tolyl vs. mesityl) and the length of the tether (4-vinylphenyl vs. 4-allylphenyl) [Zn6 and Zn7, Chart 1; Zn10 and Zn11, Chart 2]. A third set incorporates alkene-terminated tethers of different length (vinyl, allyl, 3-butenyl, 4-vinylphenyl, 4-allylphenyl) with nonlinking p-tolyl groups [Zn10-Zn14, Chart 2]. A fourth set of molecules employs a fixed tether (4-allylphenyl) and varies the size of the two flanking meso substituents (p-tolyl, methyl) and the distal meso substituent (p-tolyl, mesityl, 2,4,6-triethylphenyl) [Zn14-Zn19, Chart 3]. Two additional zinc porphyrins bear two halo or two vinyl groups at porphyrin β positions. The final porphyrin is a free base, core-modified monothia-porphyrin with two bromo groups at the β-thiophene positions. Porphyrins Zn2,[29] Zn3,[30] Zn4,[31] and Zn5[32] have been prepared previously.

Chart 1

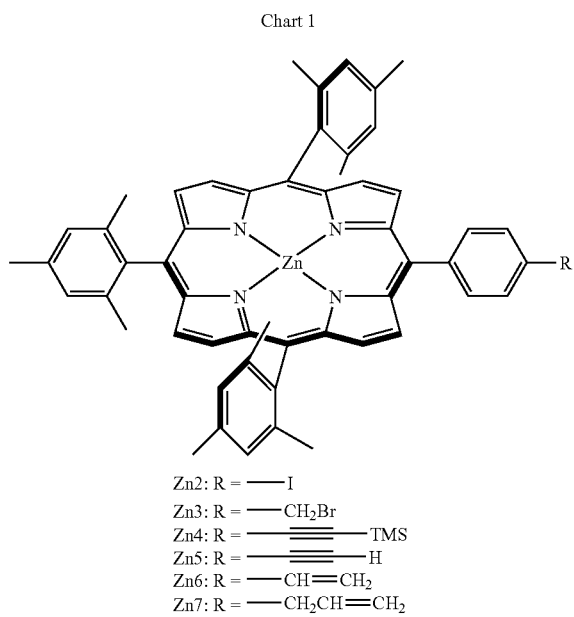

Zn2: R = —I
Zn3: R = —CH$_2$Br
Zn4: R = —≡≡—TMS
Zn5: R = —≡≡—H
Zn6: R = —CH=CH$_2$
Zn7: R = —CH$_2$CH=CH$_2$

Chart 2

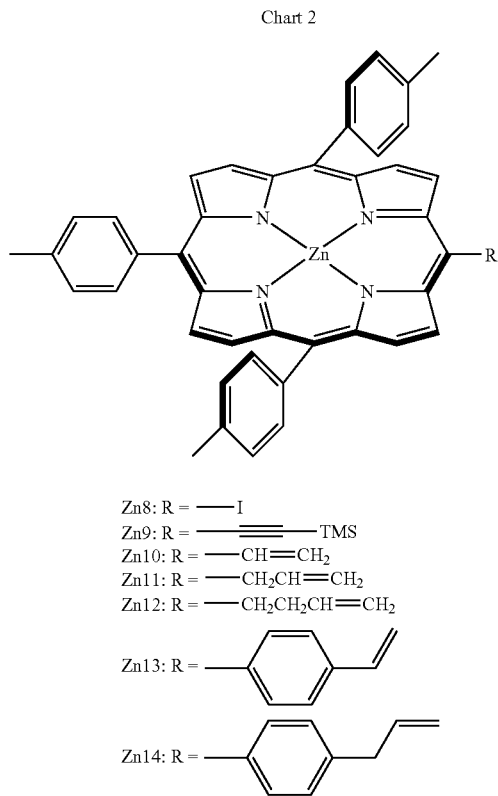

Zn8: R = —I
Zn9: R = —≡≡—TMS
Zn10: R = —CH=CH$_2$
Zn11: R = —CH$_2$CH=CH$_2$
Zn12: R = —CH$_2$CH$_2$CH=CH$_2$
Zn13: R = —⌬—CH=CH$_2$
Zn14: R = —⌬—CH$_2$CH=CH$_2$

-continued
Chart 3

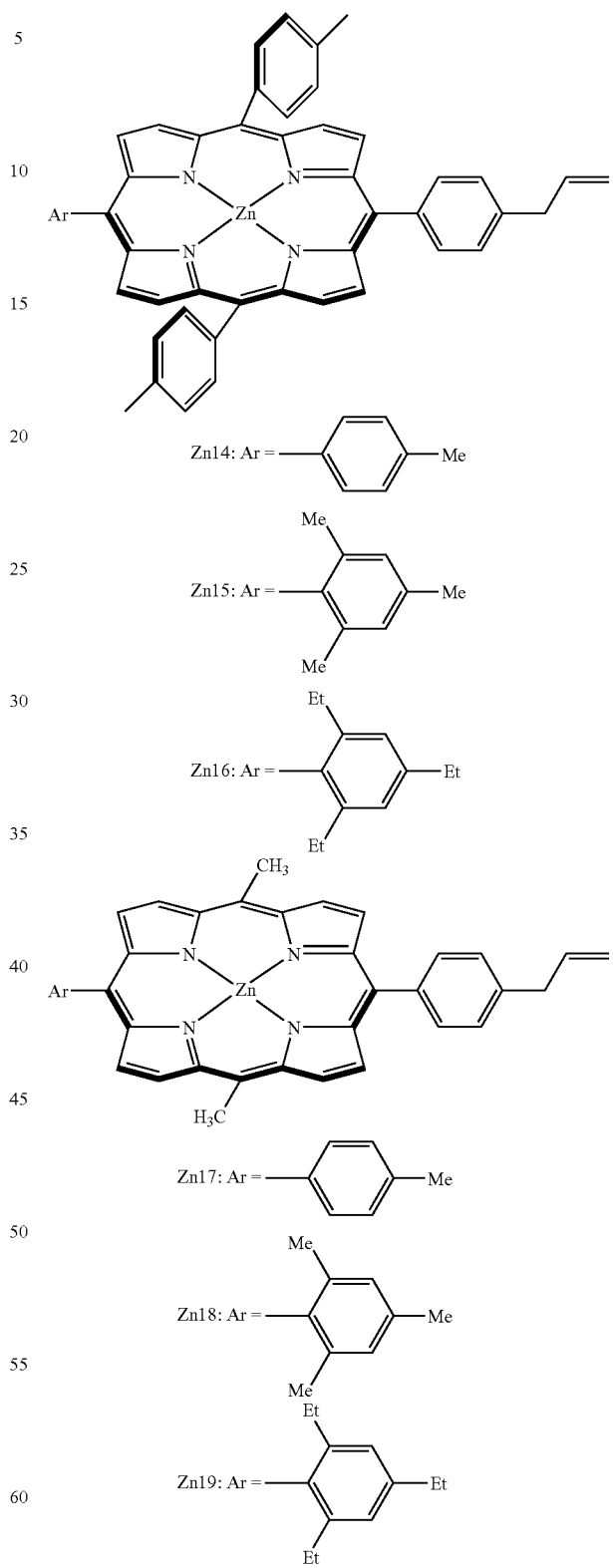

2. Synthesis of Porphyrins Bearing Meso-linked Tethers. A. Statistical Approach. Two A$_3$B-porphyrins were prepared [A=mesityl; B=4-vinylphenyl (Zn6) or 4-allylphenyl (Zn7)]

for attachment to Si(100). Porphyrins bearing three meso-mesityl groups are not available via rational synthesis but can be prepared via statistical mixed-aldehyde condensations. The synthesis of Zn6 is shown in Scheme 1. 4-Iodobenzaldehyde was protected as the dimethyl acetal (20) in 96% yield. Kumada cross-coupling[33] of 20 and vinylmagnesium bromide afforded acetal 21 in 64% yield. Removal of the acetal protecting group of 21 was not attempted given the high reactivity of the styryl moiety under either acidic or basic conditions. A mixed-aldehyde condensation[34] was carried out at elevated concentration[35] using $BF_3 \cdot O(Et)_2$-EtOH cocatalysis[36] with acetal 21, mesitaldehyde and pyrrole. Oxidation with DDQ afforded a mixture of porphyrins. The porphyrin mixture was treated with zinc acetate to give the corresponding zinc porphyrins. Porphyrins that have substituents of similar polarity but different degrees of facial encumbrance are more readily separated as the zinc chelates than as the free base forms.[31] Chromatography afforded Zn6 in 14% yield.

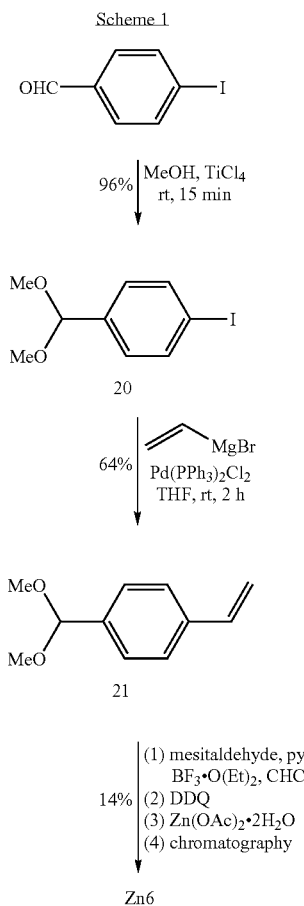

Scheme 1

Allyl-porphyrin Zn7 was prepared as shown in Scheme 2. Acetal 22[37] was treated with a biphasic solution[38] of aqueous TFA and $CH_2Cl_2$ to afford 4-allylbenzaldehyde (23) in 81% yield. A mixed-aldehyde condensation[34] of 23 with mesitaldehyde and pyrrole was carried out using $BF_3 \cdot O(Et)_2$-EtOH cocatalysis[36] followed by DDQ oxidation. Zinc insertion and chromatographic workup afforded Zn7 in 12% yield.

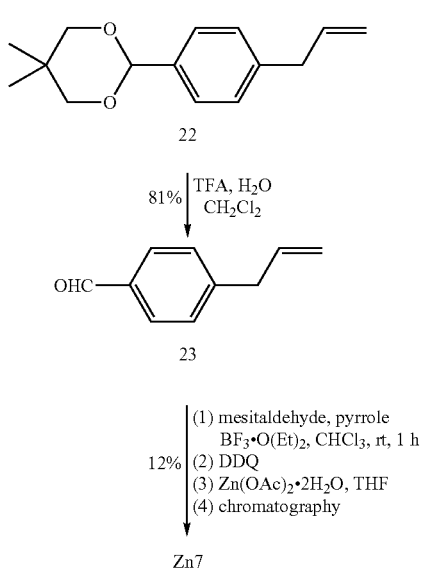

Scheme 2

B. Rational Approach. To achieve a scalable synthesis, we have investigated meso substituents that are compatible with a rational synthesis of porphyrins. The rational synthesis relies on the condensation of a dipyrromethane and a dipyrromethane-dicarbinol.[39] The synthesis of the dipyrromethanes and 1,9-diacyldipyrromethanes is described below.

Synthesis of Dipyrromethanes. The synthesis of dipyrromethanes can be achieved via the one-flask reaction of an aldehyde with excess pyrrole.[40-42] The synthetic method has generally employed TFA as the acid catalyst and workup via chromatography and Kugelrohr distillation,[41] but recently we found that milder acids could be employed in conjunction with a more simple purification procedure via direct crystallization.[42] These procedures were employed to prepare dipyrromethanes 24-31 (Scheme 3). In method A,[42] an aldehyde (21, 23, mesitaldehyde, or 4-pentenal) was condensed with pyrrole (100 eq) under $InCl_3$ (0.1 eq) catalysis at room temperature for 1.5 h, followed by quenching the reaction with powdered NaOH, filtration to remove neutralized catalyst, removal of pyrrole, and recrystallization (or column chromatography). In this manner, the new dipyrromethanes 25, 27, 28 and the known dipyrromethane 30[42] were prepared in good yields. Application of method A to 3-butenal diethyl acetal was unsuccessful. Therefore, the latter was condensed with excess pyrrole (40 eq) under TFA (0.1 eq) catalysis at room temperature for 10 min (Method B).[41] Analysis of the crude reaction mixture by GC showed a much higher percentage of N-confused dipyrromethane (25%) than is typically observed (~5%) under these conditions. Nevertheless, the two regioisomers were readily separated by column chromatography affording 24 as a viscous oil in 36% yield. The known dipyrromethanes 26[43] and 29[41] were also prepared following Method B. The condensation of 2,4,6-triethylbenzaldehyde[44] with excess pyrrole (100 eq) under $MgBr_2$ (0.5 eq) catalysis at room temperature for 1 h (Method C)[42] afforded 31 as a viscous oil in 57% yield after column chromatography. All attempts to prepare 5-vinyldipyrromethane (to serve as a precursor to porphyrin Zn10) from acrolein or acrolein diethyl acetal via method A or B were unsuccessful.

Scheme 3

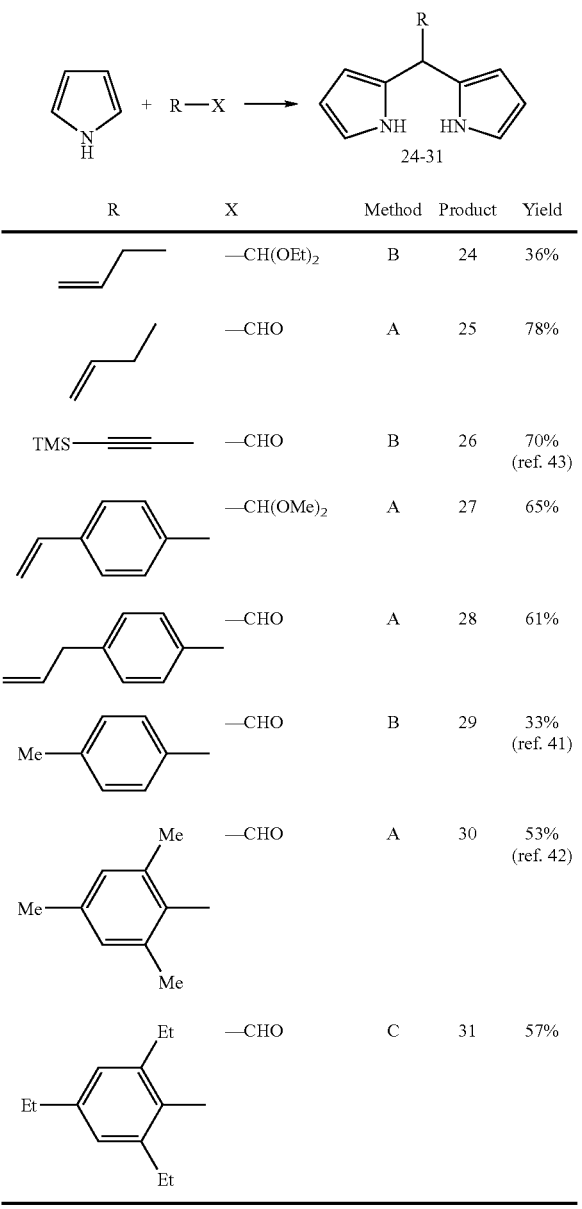

A = InCl₃ (0.1 eq), pyrrole (100 eq) rt, 1.5 h
B = TFA (0.1 eq), pyrrole (40 eq), rt, 10 min
C = MgBr₂ (0.5 eq), pyrrole (100 eq), rt, 1 h Synthesis of 1,9-Diacyldipyrromethanes. The synthesis of several 1,9-diacyldipyrromethanes is shown in Scheme 4. Treatment of a dipyrromethane with EtMgBr in toluene followed by reaction with an acid chloride typically affords a mixture of the 1-acyldipyrromethane and 1,9-diacyldipyrromethane.[39] Acyldipyrromethanes typically afford amorphous powders upon attempted crystallization and streak extensively on column chromatography. To facilitate isolation of the 1,9-diacyldipyrromethane, the crude acylation mixture is treated with dibutyltin dichloride. The diacyldipyrromethane-tin complex, which forms selectively, typically is non-polar and crystallizes readily.[45]

Scheme 4

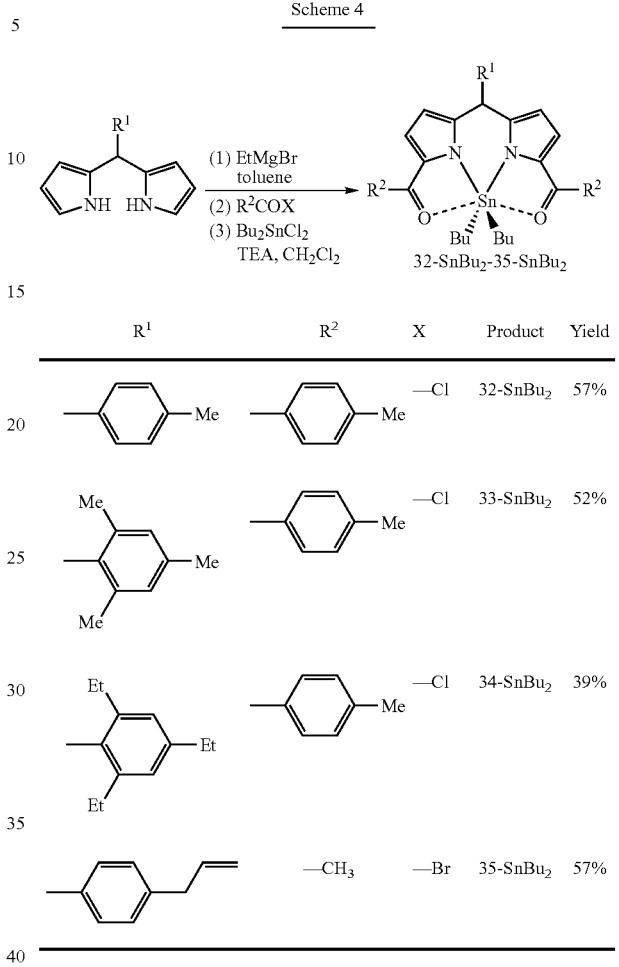

In this manner, each dipyrromethane (28-31) was separately treated with EtMgBr in toluene followed by reaction with the appropriate acid chloride (p-toluoyl chloride or acetyl bromide). Subsequent reaction with dibutyltin dichloride gave the corresponding tin complex, which was readily isolated by passage through a silica pad followed by precipitation from MeOH. The diacyldipyrromethane-tin complexes 32-SnBu₂-35-SnBu₂ were isolated in yields of 39-57%.

Synthesis of Porphyrins. The meso-substituted porphyrins Zn9 and Zn11-Zn19 were prepared by reaction of a dipyrromethane and a dipyrromethane-dicarbinol (Scheme 5). The dipyrromethane-dicarbinols were prepared by reduction with NaBH₄ of the corresponding 1,9-diacyldipyrromethane-tin complex[45] or of the unsubstituted 1,9-diacyldipyrromethane.[39] The complete reduction of the tin(IV) complexes requires a slightly longer reaction time (~2 h) versus that of the uncomplexed diacyldipyrromethane (40 min). The dipyrromethane+dipyrromethane-dicarbinol condensation was performed at room temperature with catalysis by TFA (30 mM) in CH₃CN[39] or Yb(OTf)₃ (3.2 mM) in CH₂Cl₂.[i] Subsequent oxidation with DDQ and zinc metalation afforded the target porphyrin.

Scheme 5

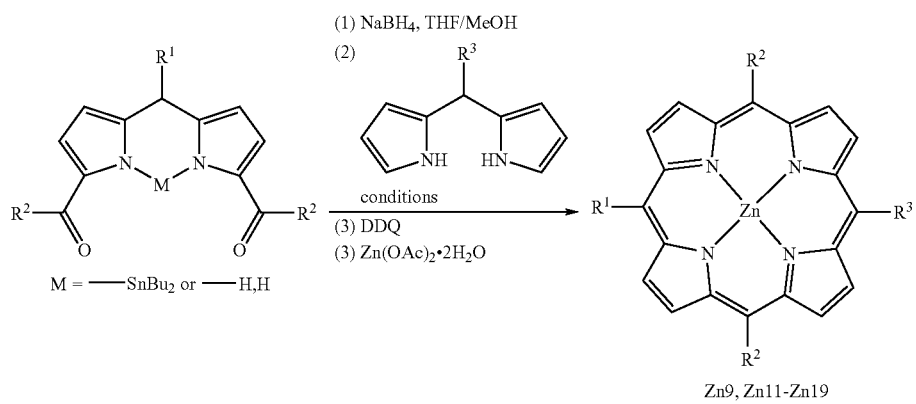

| Entry | Components | R¹ | R² | R³ | Conditions | Product | Yield |
|---|---|---|---|---|---|---|---|
| 1 | 32 + 26 | -C₆H₄-Me (p-tolyl) | -C₆H₄-Me (p-tolyl) | —≡—TMS | A | Zn9 | 13% |
| 2 | 32-SnBu₂ + 24 | -C₆H₄-Me (p-tolyl) | -C₆H₄-Me (p-tolyl) | allyl (-CH₂CH=CH₂) | B | Zn11 | 44% |
| 3 | 32-SnBu₂ + 25 | -C₆H₄-Me (p-tolyl) | -C₆H₄-Me (p-tolyl) | -(CH₂)₃CH=CH₂ | B | Zn12 | 42% |
| 4 | 32 + 27 | -C₆H₄-Me (p-tolyl) | -C₆H₄-Me (p-tolyl) | -C₆H₄-CH=CH₂ | A | Zn13 | 26% |
| 5 | 32-SnBu₂ + 28 | -C₆H₄-Me (p-tolyl) | -C₆H₄-Me (p-tolyl) | -C₆H₄-CH₂CH=CH₂ | B | Zn14 | 23% |
| 6 | 33-SnBu₂ + 28 | mesityl (2,4,6-Me₃C₆H₂) | -C₆H₄-Me (p-tolyl) | -C₆H₄-CH₂CH=CH₂ | B | Zn15 | 21% |
| 7 | 34-SnBu₂ + 28 | 2,4,6-Et₃C₆H₂ | -C₆H₄-Me (p-tolyl) | -C₆H₄-CH₂CH=CH₂ | B | Zn16 | 10% |

| Entry | Components | R³ | R² | R¹ | Conditions | Product | Yield |
|---|---|---|---|---|---|---|---|
| 8 | 35-SnBu₂ + 29 | -C₆H₄-Me (p-tolyl) | —CH₃ | -C₆H₄-CH=CH₂ | B | Zn17 | 15% |

-continued

Scheme 5

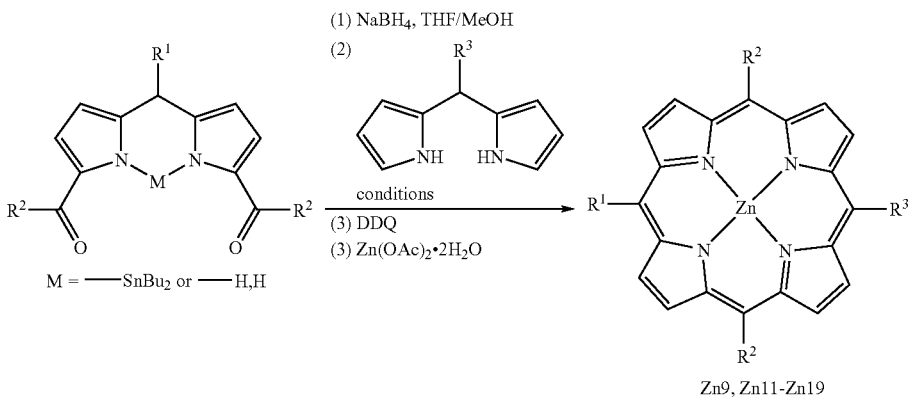

| 9 | 35-SnBu₂ + 30 | Me, Me, Me (2,4,6-trimethylphenyl) | —CH₃ | p-tolyl-CH=CH₂ | B | Zn18 | 19% |
| 10 | 35-SnBu₂ + 31 | Et, Et, Et (2,4,6-triethylphenyl) | —CH₃ | p-tolyl-CH=CH₂ | B | Zn19 | 9% |

A = TFA, MeCN, rt
B = Yb(OTf)₃, CH₂Cl₂, rt

The use of mild Lewis acids in $CH_2Cl_2$ generally affords slightly higher yields and a more facile workup than use of TFA in $CH_3CN$. However, attempts to prepare Zn9 (Entry 1) using either $InCl_3$ or $Yb(OTf)_3$ gave lower yields (3-11%) than with TFA (13%). The yields of porphyrins Zn16 and Zn19 were somewhat low (~10%), which is attributed to the bulky 2,4,6-triethylphenyl moiety. Also, porphyrins bearing meso-methyl groups (Entries 8-10) gave lower yields than the analogous porphyrins bearing meso-p-tolyl groups (Entries 5-7). In each case, the porphyrin-forming reaction was rapid (<30 min). Analysis by laser desorption mass spectrometry (LDMS)[47] of the crude reaction mixtures after bulk oxidation showed no evidence of the presence of any other porphyrin species.

One porphyrin that was not available via this route was the vinyl-porphyrin Zn10, owing to the lack of access to 5-vinyl-dipyrromethane (vide supra). The synthesis of Zn10 was achieved following the route outlined in Scheme 6. Diacyldipyrromethane 32[48] was reduced with $NaBH_4$ and the resulting 32-diol was condensed with dipyrromethane (36)[41,49] in $CH_2Cl_2$ containing $Yb(OTf)_3$ at room temperature. Subsequent oxidation with DDQ afforded free base porphyrin 37 in 33% yield. Porphyrin 37 was iodinated at the meso-position using $I_2$ and $(CF_3CO_2)_2IC_6H_5$ in $CHCl_3$/pyridine[50] to furnish free base porphyrin 8 in 82% yield. Zinc insertion afforded Zn8 in 75% yield. Porphyrin Zn8 was then subjected to a Stille cross-coupling reaction[51] with (vinyl)tributyltin and $Pd(PPh_3)_4$ to afford vinylporphyrin Zn10 in 77% yield.

Scheme 6

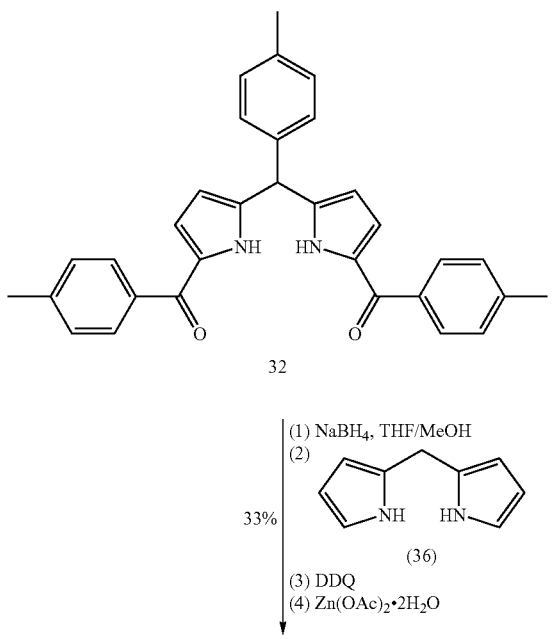

-continued

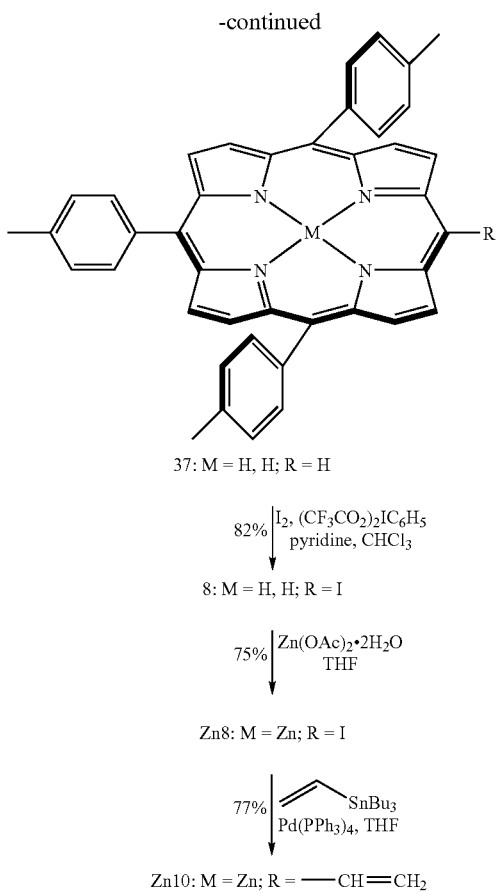

37: M = H, H; R = H

82% | $I_2$, $(CF_3CO_2)_2IC_6H_5$
pyridine, $CHCl_3$

8: M = H, H; R = I

75% | $Zn(OAc)_2 \cdot 2H_2O$
THF

Zn8: M = Zn; R = I

77% | $\diagup\!\!\!\diagdown SnBu_3$
$Pd(PPh_3)_4$, THF

Zn10: M = Zn; R = ——CH=$CH_2$

3. Attachment Methods. Baking. The initial high-temperature attachment procedure involved a direct deposition approach. In this procedure, the porphyrin was first dissolved in an organic solvent and a small drop (1 µL) of the resulting dilute solution was placed onto a micron-size Si microelectrode that was contained in a sealed vial maintained under inert atmosphere (see Experimental Section for additional details). The vial was then placed on a hot plate preheated to a particular temperature and the system was "baked" for a specified time. The Si platform was then cooled, washed to remove non-attached porphyrin, and interrogated voltammetrically to investigate the quality of the monolayer and determine the surface coverage (by integration of the peaks in the voltammogram).

The "best" attachment conditions for direct deposition were determined via a systematic study using porphyrins Zn1 and Zn7 that probed the effects of varying the baking temperature, the baking time, the concentration of the porphyrins in the deposition solution, and the nature of the deposition solvent. The first three of these variables are not independent; however, the studies revealed the following general trends: (1) As the baking temperature is increased, the surface coverage monotonically increases. For example, increasing the baking temperature from 100 to 400° C. (baking time 30 min; deposition solution porphyrin conc. 1 mM) increased the surface concentration from $1\times10^{-11}$ mol $cm^{-2}$ to $\sim 8\times10^{-11}$ mol $cm^{-2}$ (the saturating coverage for the porphyrin is $\sim 10^{-10}$ mol $cm^{-2}$). At temperatures above 400° C., no further attachment is achieved and the system degrades. (2) As the baking temperature is increased, the time required to achieve the highest surface coverage monotonically decreases. For example, a baking time of 1 h was required to achieve maximum coverage at 200° C. This time was reduced to 2 min when the baking temperature was elevated to 400° C. (3) As the concentration of the porphyrin in the deposition solution was increased from 1 µM to 100 µM, the surface coverage for a given baking time and temperature systematically increased. Increasing the porphyrin concentrations above 100 µM had little effect on the coverage. (4) Both high-boiling (benzonitrile, bp=191° C.) and low-boiling (THF, bp=66° C.) solvents yielded essentially identical results for a particular set of deposition and baking conditions. The best conditions were applied to several porphyrins. FIG. 1 (top panels) shows representative cyclic voltammograms of Zn1 and Zn7 obtained by attaching the porphyrins using a 100 µM deposition solution followed by baking at 400° C. for 2 min.

Sublimation. The next high-temperature attachment procedure involved an indirect deposition approach. In this procedure, a small quantity of the porphyrin (<1 mg) was placed in the bottom of a cylindrical glass container whose diameter permitted insertion into the heating vial. The top of the container was flat to allow the Si platform to be placed on top with the micron-size electrode facing downward (~3 mm above the solid sample). The vial was sealed, purged with Ar, placed on a hot plate preheated to a particular temperature, and the porphyrin was sublimed for a specified time. The Si platform was then cooled, washed to remove non-attached porphyrin, and interrogated voltammetrically to investigate the quality of the monolayer and determine the surface coverage. Representative cyclic voltammograms of Zn1 and Zn7 are shown in FIG. 1 (bottom panels). Both of these molecules were attached by subliming at 400° C. for 20 min. The "best" attachment conditions for indirect deposition were determined via a systematic study that probed the effects of varying the sublimation temperature and baking time. At temperatures below 300° C., relatively little attachment was achieved via the sublimation method. At 400° C., the surface coverage monotonically increased as the sublimation time was increased. No further coverage was observed for times longer than 20 min. It is noteworthy that while sublimation of porphyrinic compounds is a well-known process for purification and for generation of thin films,[56] the sublimation process developed herein employs porphyrins bearing a reactive tether and enables fabrication of surface-attached monolayers of the porphyrins.

Scope of Application. With the baking and sublimation methods in hand for attachment of porphyrins to Si, porphyrins Zn1-Zn19 were examined for attachment using the same deposition conditions (baking temperature 400° C.; baking time 2 min; deposition solution porphyrin conc. 1 mM). The functional groups that afforded attachment include 2-(trimethylsilyl)ethynyl, vinyl, allyl, and 3-butenyl directly appended to the porphyrin, and iodo, bromomethyl, 2-(trimethylsilyl)ethynyl, ethynyl, vinyl, and allyl appended to the 4-position of a meso-phenyl ring. The surface coverage varied somewhat as a function of porphyrin and/or linker type; however the surface coverages were typically in the range $4\times10^{-11}$ mole $cm^{-2}$ to $8\times10^{-11}$ mol $cm^{-2}$. Attachment was not achieved for Zn8. In general, the surface coverages and characteristic features of the voltammograms obtained via the sublimation method (sublimation temperature 400° C.; sublimation time 20 min) are quite similar to those obtained via the baking method, indicating covalent attachment and robust electrochemical behavior.[6] The relatively narrow voltammetric waves and the absence of visible surface oxidation at high potentials suggest that the porphyrins are packed relatively uniformly and fully cover the surface. As controls, the zinc chelates of various porphyrins that lack functional groups were examined, including 2,3,7,8,12,13,17,18-octaethylporphyrin, meso-tetraphenylporphyrin, meso-tetra-p-tolylporphyrin, and meso-tetramesitylporphyrin. No attachment was observed for any of these porphyrins as was evident from the observation that the baked film was completely removed by washing (in addition, no voltammetric peaks were observed). Collectively, these results indicate that the high-temperature attachment procedure (1) has broad scope encompassing diverse functional groups, (2) tolerates a variety of arene substituents, and (3) does not afford indiscriminate attachment. Finally, the Zn7 monolayer was used in an initial series of tests to evaluate the robustness to electrochemical cycling of the carbosilane tethered porphyrins. This test was conducted as described in ref 4 and showed that the voltammetric characteristics of the monolayer were unchanged after ~$10^{10}$ redox cycles.

Outlook. We have prepared a set of porphyrins bearing carbon tethers for attachment to Si(100). Collectively, the studies reported herein indicate that porphyrins bearing a variety of functional groups can be covalently attached to Si via high-temperature processing. The baking and sublimation methods are complementary and together afford a nearly universal strategy for attaching porphyrins. The baking method employs the porphyrin in a dilute solution (1 µM-1 mM) while the sublimation method employs the porphyrin as a neat solid. We note that the success of both approaches apparently does not depend on melting the porphyrins. Indeed, the melting points of the porphyrins ranged from 230° C. (Zn19) to 435° C. (Zn14) yet good quality monolayers were obtained regardless of melting point value. The baking approach is essentially "dry" inasmuch as only a small amount of solvent is used in the attachment process; the sublimation approach is totally "dry" in that no solvents are required in the process. This latter process is particularly appealing from a semiconductor processing perspective, wherein uniform attachment of molecules to very large (30 cm) Si wafers might be anticipated in the manufacture of future-generation hybrid molecular/semiconductor devices.

Experimental Section

A. Electrochemical Studies and Attachment Procedure. The porphyrins were attached to Si microelectrodes (100 µm×100 µm) that were prepared photolithographically from device-grade wafers (B-doped Si(100); $\rho$=0.005–0.1 Ωcm). The procedure for preparing these microelectrodes is described in detail in ref 6. The electrochemical procedures, techniques, and instrumentation were also the same as described in ref 6. The surface coverage of the molecules was determined by integrating the peaks in the voltammogram. The temperature of the Si platform was measured by attaching a thermocouple directly to the platform.

The basic procedures for attachment via the baking and sublimation methods are as described in the Results and Discussion. Additional details of these procedures are described below.

For the baking procedure, porphyrin concentrations in the range 1 µM to 3 mM were investigated. The solvents included benzonitrile, THF, and $CH_2Cl_2$. The choice of solvent was primarily dictated by solubility of the porphyrin rather than any specific characteristics of the solvent. However, monolayers prepared using benzonitrile or THF exhibited superior voltammetric characteristics relative to those prepared using $CH_2Cl_2$, likely due to the fact that the halogenated solvent can react with the surface at high temperature.

Prior to introduction of the porphyrin and baking, the Si microelectrode was placed in a vial. The vial was sealed with a teflon cap and purged with Ar for 15 min. A syringe containing the porphyrin solution was inserted through the teflon cap and a drop of the solution was placed onto the microelectrode. The solvent was then allowed to dry under the continued Ar purge. The purge was stopped, the vial was transferred to the hot plate at the preset temperature, and the electrode was baked for a specified time. The temperatures investigated ranged from 200 to 450° C.; the times ranged from 2 to 30 min. The vial was then removed from the hot plate and the Ar purge was reinitiated. After the vial had reached room temperature, solvent was syringed into the vial to wash the electrode and remove non-attached porphyrin. In some cases, the microelectrode was removed from the vial and washed in air. No difference was observed in the voltammetric characteristics of the monolayers for electrodes washed under inert versus ambient conditions.

For the sublimation procedure, the vessel containing the solid porphyrin was placed into the vial, the microelectrode was placed on top of the vessel, and the vial was sealed. The vial was then purged gently (to prevent displacing the microelectrode from the vessel) for 15 min. The purge was stopped and the vial was transferred to the hot plate at the preset temperature for a specific time. Times in the range 2 to 20 min were investigated. The vial was then removed from the hot plate and allowed to cool to room temperature. The microelectrode was then removed and washed to remove non-attached porphyrin.

B. Compound Synthesis.

General. $^1H$ (300 or 400 MHz) and $^{13}C$ (75 MHz) NMR spectra were recorded in $CDCl_3$ unless noted otherwise. Mass spectra of porphyrins were obtained by laser desorption mass spectrometry in the absence of a matrix (LDMS) and by high-resolution fast atom bombardment mass spectrometry (FABMS). Absorption and emission spectra were collected in toluene at room temperature. Elemental analyses were performed by Atlantic Microlab, Inc. Melting points are uncorrected. For porphyrins, a melting point onset value is given. Silica gel (Baker 40 µm average particle size) was used for column chromatography. Chloroform contained 0.8% ethanol as a stabilizer. The presence of ethanol in chloroform enables $BF_3$-ethanol cocatalysis in reactions with mesitaldehyde and pyrrole. The citations in the following sections refer to those listed in the body of the paper.

Melting Point Study. Each porphyrin was subjected to a melting-point determination. In a few cases, relatively sharp melting points (ΔT=5-6° C.) were observed. In most cases, the mp range was partially obscured (owing to concurrent sublimation and the intense optical density of the sample). For consistency, the value for the mp onset of each compound is reported. The mp onset values are as follows: Zn1 (275° C.); Zn2 (285° C.); Zn3 (dec. at 400° C.); Zn4 (260° C.); Zn5 (245° C.); Zn6 (270° C.); Zn7 (255° C.); Zn8 (425° C.); Zn9 (380° C.); Zn10 (370° C.); Zn11 (350° C.); Zn12 (350° C.); Zn13 (430° C.); Zn14 (435° C.); Zn15 (340° C.); Zn16 (250° C.); Zn17 (335° C.); Zn18 (290° C.); Zn19 (230° C.); Zn40 (>300° C.); Zn41 (310° C.); 45 (>450° C.).

Noncommercial Compounds. Compounds Zn1,[6] Zn2,[29] Zn3,[30] Zn4,[31] Zn5,[32] 22,[37] 2,4,6-triethylbenzaldehyde,[44] 26,[43] 29,[41] 30,[42] 32,[48] 36,[41,49] 38,[52] and 44[55] were prepared as described in the literature.

Zn(II)-5,10,15-Trimesityl-5-(4-vinylphenyl)porphyrin (Zn6). Following a standard procedure for mixed-aldehyde condensation[34] at high concentration[35] with $BF_3.O(Et)_2$-ethanol cocatalysis,[36] samples of 21 (500 mg, 2.81 mmol), mesitaldehyde (1.24 mL, 8.42 mmol), and pyrrole (779 µL, 11.2 mmol) were condensed in $CHCl_3$ (153 mL) in the presence of $BF_3.O(Et)_2$ (347 µL, 2.74 mmol) at room temperature for 1 h. Then DDQ (1.91 g, 8.42 mmol) was added. After 10 min, the crude mixture was passed through a silica column (CH$_2$Cl$_2$) to recover the mixture of porphyrins free from polar byproducts. A solution of the porphyrin mixture in CHCl$_3$ (150 mL) was treated with a solution of Zn(OAc)$_2$.2H$_2$O (1.53 g, 7.00 mmol) in MeOH (20 mL). After 15 h, the solution was washed with water. Column chromatography [silica, CHCl$_3$/hexanes (11:9) followed by silica, CHCl$_3$/hexanes (1:2)] afforded a purple solid (330 mg, 14%): mp onset 270° C.; $^1$H NMR δ 1.85 (s, 12H), 1.87 (s, 6H), 2.63 (s, 9H), 5.48 (d, J=10.0 Hz, 1H), 6.08 (d, J=16.8 Hz, 1H), 7.07 (dd, J$^1$=16.8 Hz, J$^2$=10.0 Hz, 1H), 7.31 (s, 6H), 7.82 (d, J=9.6 Hz, 2H), 8.21 (d, J=9.6 Hz, 2H), 8.70-8.79 (m, 6H), 8.92 (d, J=5.4 Hz, 2H); LDMS obsd 829.4; FABMS obsd 828.3176, calcd 828.3170 (C$_{55}$H$_{48}$N$_4$Zn); λ$_{abs}$ 423, 512, 550, 588 nm.

Zn(II)-5-(4-Allylphenyl)-10,15,20-trimesitylporphyrin (Zn7). Following the procedure for Zn6, reaction of 23 (365 mg, 2.50 mmol), mesitaldehyde (1.11 g, 7.50 mmol), and pyrrole (672 mg, 10.0 mmol) was carried out in CHCl$_3$ (1.0 L) in the presence of BF$_3$.O(Et)$_2$ (1.32 mL of a 2.5 M solution in CHCl$_3$) at room temperature for 1 h followed by oxidation with DDQ (1.70 g, 7.50 mmol) and passage through a silica pad [CH$_2$Cl$_2$/hexanes, (1:1)]. The mixture of porphyrins was dissolved in THF (250 mL) and treated with Zn(OAc)$_2$.2H$_2$O (450 mg, 2.10 mmol) at 50° C. for 4 h and then overnight at room temperature. The volume of THF was reduced to 50 mL and the mixture of zinc porphyrins was precipitated upon addition of methanol. Chromatography [silica, toluene/hexanes, (1:2.5)] followed by crystallization (CH$_2$Cl$_2$/MeOH) gave pink crystals (250 mg, 12%): mp onset 255° C.; $^1$H NMR δ 1.83 (s, 18H), 2.63 (s, 9H), 3.75 (d, J=6.4 Hz 2H), 5.30 (m, 2H), 6.29-6.32 (m, 1H), 7.26 (s, 6H), 7.55 (d, J=7.2 Hz, 2H), 8.13 (d, J=8.0 Hz, 2H), 8.69 (s, 4H), 8.73 (d, J=4.8 Hz, 2H), 8.87 (d, J=4.8 Hz, 2H); LDMS obsd 842.97; FABMS obsd 842.3365, calcd 842.3327 (C$_{56}$H$_{50}$N$_4$Zn); λ$_{abs}$ 421, 551, 593 nm.

5-Iodo-10,15,20-tri-p-tolylporphyrin (8). Following a standard method,[50] a solution of 37 (871 mg, 1.50 mmol) and I$_2$ (267 mg, 1.05 mmol) in CHCl$_3$ (210 mL) was treated with a solution of [bis(trifluoroacetoxy)iodo]benzene (478 mg, 1.20 mmol) in CHCl$_3$ (30 mL) followed by pyridine (1.3 mL). The mixture was stirred at room temperature for 1 h. The reaction mixture was diluted with CH$_2$Cl$_2$, washed with aqueous Na$_2$S$_2$O$_3$, water and dried (Na$_2$SO$_4$). After concentrating the solution to a volume of ~100 mL, 30 mL of hexanes was added. The resulting purple precipitate was filtered, washed (CH$_2$Cl$_2$, hexanes) and dried to yield the free base porphyrin (618 mg). The filtrate was concentrated and chromatographed (silica gel, warm toluene/hexanes=7:3), affording additional free base porphyrin (253 mg). The total yield is 871 mg (82%): $^1$H NMR δ -2.70 (s, 2H), 2.69-2.74 (brs, 9H), 7.53-7.59 (br m, 6H), 8.04-8.09 (br m, 6H), 8.78-8.83 (m, 4H), 8.89 (d, J=4.8 Hz, 2H), 9.67 (d, J=4.4 Hz, 2H); LDMS obsd 706.9; FABMS obsd 706.1613, calcd 706.1593 (C$_{41}$H$_{31}$IN$_4$); λ$_{abs}$ 424, 520, 557, 598, 656 nm.

Zn(II)-5-Iodo-10,15,20-tri-p-tolylporphyrin (Zn8). A solution of 8 (353 mg, 0.500 mmol) in THF (60 mL) was treated with Zn(OAc)$_2$.2H$_2$O (1.10 g, 5.00 mmol) at room temperature for 8 h. After removal of the solvent, the residue was chromatographed (silica gel, hexanes/CH$_2$Cl$_2$, (1:1)] affording a powder that was recrystallized [(hexanes/CH$_2$Cl$_2$), 349 mg, 91%]: mp onset 425° C.; $^1$H NMR δ 2.67-2.70 (br s, 9H), 7.53-7.59 (br m, 6H), 8.01-8.06 (br m, 6H), 8.79 (m, 4H), 8.87 (d, J=5.6 Hz, 2H), 9.72 (d, J=4.4 Hz, 2H); LDMS obsd 770.5; FABMS obsd 768.0760, calcd 768.0728 (C$_{41}$H$_{29}$IN$_4$Zn); λ$_{abs}$ 429, 519, 556, 596 nm.

Zn(II)-5-[2-(Trimethylsilyl)ethynyl]-10,15,20-tri-p-tolylporphyrin (Zn9). A sample of 32 (473 mg, 1.00 mmol) was reduced following a general procedure[39] and the resulting 32-diol was condensed with 26 (243 mg, 1.00 mmol) in CH$_3$CN (400 mL) under TFA (930 μL, 12.1 mmol) catalysis at room temperature for 4 min. Then DDQ (681 mg, 3.00 mmol) was added. After 1 h, TEA (2 mL) was added. The mixture was concentrated and the residue was chromatographed [silica gel, hexanes/CH$_2$Cl$_2$, (3:7)] affording the free base porphyrin (116 mg, 17%): mp onset 380° C.; $^1$H NMR δ -2.41 (s, 2H), 0.62 (s, 9H), 2.71 (s, 3H), 2.72 (s, 6H), 7.54 (d, J=8.0 Hz, 2H), 7.57 (d, J=8.0 Hz, 4H), 8.05 (d, J=8.0 Hz, 2H), 8.08 (d, J=8.0 Hz, 4H), 8.79 (s, 4H), 8.92 (d, J=4.4 Hz, 2H), 9.65 (d, J=4.8 Hz, 2H); LDMS obsd 676.2; FABMS obsd 676.3047, calcd 676.3022 (C$_{46}$H$_{40}$N$_4$Si); λ$_{abs}$ 431, 497, 529, 567, 606, 664 nm. A sample of the free base porphyrin (169 mg, 0.250 mmol) in THF (25 mL) was treated with a solution of Zn(OAc)$_2$.2H$_2$O (275 mg, 1.25 mmol) in MeOH (2 mL) at room temperature for 12 h. Column chromatography [hexanes/CH$_2$Cl$_2$, (3:7)] afforded a purple solid (136 mg, 74%; 13% overall yield): $^1$H NMR δ 0.62 (s, 9H), 2.70-2.73 (br s, 9H), 7.53-7.59 (m, 6H), 8.04-8.10 (m, 6H), 8.79 (s, 4H), 8.92 (m, 2H), 9.65 (m, 2H); LDMS obsd 739.8; FABMS obsd 738.2167, calcd 738.2157 (C$_{46}$H$_{38}$N$_4$SiZn); λ$_{abs}$ 434, 523, 563, 605 nm.

Zn(II)-5,10,15-Tri-p-tolyl-20-vinylporphyrin (Zn10). A solution of Zn8 (50 mg, 60 μmol) in THF (24 mL) was treated overnight with Pd(PPh$_3$)$_4$ (7 mg) and tributyl(vinyl)tin (190 μL, 600 μmol) at 60° C. under argon. The reaction mixture was concentrated. Column chromatography [silica, CH$_2$Cl$_2$/hexanes (1:1)] followed by trituration of the product with hexanes afforded a purple solid (34 mg, 77%): mp onset 370° C.; $^1$H NMR δ 2.72 (s, 3H), 2.74 (s, 6H), 6.05 (d, J=17.6 Hz, 1H), 6.49 (d, J=11.6 Hz, 1H), 7.55-7.58 (m, 6H), 8.08-8.10 (m, 6H), 8.95 (s, 4H), 8.99 (d, J=4.4 Hz, 2H), 9.16-9.23 (m, 1H), 9.51 (d, J=4.4 Hz, 2H); LDMS obsd 668.8; FABMS obsd 668.1928, calcd 668.1918 (C$_{43}$H$_{32}$N$_4$Zn); λ$_{abs}$ 426, 554, 595 nm.

Zn(II)-5-Allyl-10,15,20-tri-p-tolylporphyrin (Zn11). A sample of 32-SnBu$_2$ (500 mg, 0.711 mmol) was reduced following a general procedure[39] and the resulting 32-diol was condensed with 24 (132 mg, 0.711 mmol) in CH$_2$Cl$_2$ (264 mL) containing Yb(OTf)$_3$ (564 mg, 0.910 mmol) at room temperature for 7 min. Then DDQ (3 equiv per dipyrromethane; 484 mg, 2.13 mmol) was added. The reaction mixture was passed over a silica column (CH$_2$Cl$_2$). The resulting free base porphyrin was dissolved in CHCl$_3$ (50 mL) and treated with a solution of Zn(OAc)$_2$.2H$_2$O (780 mg, 3.6 mmol) in MeOH (7 mL) at room temperature for 2 h. Column chromatography (silica, CHCl$_3$) afforded a purple solid (207 mg, 42%): mp onset 350° C.; $^1$H NMR δ 2.71 (s, 3H), 2.73 (s, 6H), 5.18-5.22 (m, 2H), 5.77 (d, 2H), 6.88 (m, 1H), 7.53-7.57 (m, 6H), 8.07-8.10 (m, 6H), 8.92 (s, 4H), 9.00 (d, J=4.4 Hz, 2H), 9.53 (d, J=4.4 Hz, 2H); LDMS obsd 681.3; FABMS obsd 682.2084, calcd 682.2075 (C$_{44}$H$_{34}$N$_4$Zn); λ$_{abs}$ 424, 552, 592 nm.

Zn(II)-5-(3-Butenyl)-10,15,20-tri-p-tolylporphyrin (Zn12). Following the procedure for Zn11, the condensation of 32-diol (derived from 32-SnBu$_2$; 500 mg, 0.711 mmol) and 25 (142 mg, 0.711 mmol) for 7 min, oxidation with DDQ, passage through a silica pad (CH$_2$Cl$_2$), and metalation with Zn(OAc)$_2$.2H$_2$O followed by chromatography (silica, CHCl$_3$) afforded a purple solid (213 mg, 44%): mp onset 300° C.; $^1$H NMR δ 2.71 (s, 3H), 2.73 (s, 6H), 3.32 (m, 2H), 5.07-5.17 (m, 3H), 5.77 (d, 1H), 6.29 (m, 1H), 7.54-7.58 (m, 6H), 8.07-8.10 (m, 6H), 8.92 (s, 4H), 9.01 (d, J=4.4 Hz, 2H), 9.52 (d, J=4.4 Hz, 2H); LDMS obsd 697.1, 656.0 [(M-allyl)$^+$]; FABMS obsd 696.2203, calcd 696.2231 (C$_{45}$H$_{36}$N$_4$Zn); λ$_{abs}$ 424, 513, 552, 591 nm.

Zn(II)-5,10,15-Tri-p-tolyl-20-(4-vinylphenyl)porphyrin (Zn13). Following the procedure for Zn9, the reaction of 32-diol (derived from 32; 600 mg, 1.27 mmol) and 27 (315 mg, 1.27 mmol) in MeCN (508 mL) containing TFA (1.17 mL, 15.2 mmol) for 3 min followed by oxidation with DDQ (865 mg, 3.81 mmol), neutralization with TEA (1 mL), and passage through a silica pad ($CH_2Cl_2$) afforded the partially purified free base porphyrin. Metalation in $CHCl_3$ (150 mL) with $Zn(OAc)_2 \cdot 2H_2O$ (640 mg, 2.92 mmol) in MeOH (15 mL) for 1 h and the standard workup including washing with MeOH furnished a purple solid (242 mg, 26%): mp onset 430° C.; $^1H$ NMR δ 2.67 (s, 9H), 5.48 (d, J=10.0 Hz, 1H), 6.11 (d, J=16.8 Hz, 1H), 7.10 (dd, $J^1$=16.8 Hz, $J^2$=10.0 Hz, 1H), 7.60 (d, J=8.4 Hz, 6H), 7.82 (d, J=8.4 Hz, 2H), 8.11 (d, J=8.4 Hz, 6H), 8.21 (d, J=8.4 Hz, 2H), 8.99-9.01 (m, 8H); LDMS obsd 745.2; FABMS obsd 744.2233, calcd 744.2231 ($C_{49}H_{36}N_4Zn$); $\lambda_{abs}$ 425, 551, 592 nm.

Zn(II)-5-(4-Allylphenyl)-10,15,20-tri-p-tolylporphyrin (Zn14). Following the procedure for Zn11, the condensation of 32-diol (derived from 32-$SnBu_2$; 2.00 g, 2.84 mmol) and 28 (745 mg, 2.84 mmol) for 15 min, oxidation with DDQ (1.93 g, 8.52 mmol) and passage through a silica pad ($CH_2Cl_2$) afforded the free base porphyrin, which was suspended in ethanol/hexanes (1:1), sonicated for 5 min and then centrifuged. The ethanol/hexanes mixture was decanted and the solid was dried affording the free base porphyrin (14) (455 mg, 23%): mp onset 435° C.; $^1H$ NMR δ −2.77 (brs, 2H), 2.71 (s, 9H), 3.75 (d, J=7.8 Hz, 2H), 5.27-5.37 (m, 2H), 6.26-6.33 (m, 1H), 7.55-7.58 (m, 8H), 8.10-8.16 (m, 8H), 8.86 (s, 8H); LDMS obsd 697.4; FABMS obsd 696.3265, calcd 696.3253 ($C_{50}H_{40}N_4$). Metalation of the free base porphyrin (100 mg, 0.143 mmol) in $CHCl_3$ (15 mL) with $Zn(OAc)_2 \cdot 2H_2O$ (157 mg, 0.717 mmol) in MeOH (2 mL) for 18 h followed by standard workup and chromatography (silica, $CHCl_3$) afforded a purple solid (106 mg, 97%): $^1H$ NMR δ 2.72 (s, 9H), 3.76 (d, J=7.8 Hz, 2H), 5.27-5.38 (m, 2H), 6.25-6.35 (m, 1H), 7.55-7.58 (m, 8H), 8.10 (d, J=7.6 Hz, 6H), 8.14 (d, J=8.0 Hz, 2H), 8.97 (s, 8H); LDMS obsd 759.4; FABMS obsd 758.2429, calcd 758.2388 ($C_{50}H_{38}N_4Zn$); $\lambda_{abs}$ 424, 511, 550, 591 nm.

Zn(II)-5-(4-Allylphenyl)-15-mesityl-10,20-di-p-tolylporphyrin (Zn15). Following the procedure for Zn11, the condensation of 33-diol (derived from 33-$SnBu_2$; 699 mg, 0.953 mmol) and 28 (250 mg, 0.953 mmol) for 15 min, oxidation with DDQ (649 mg, 2.86 mmol), passage through a silica pad ($CH_2Cl_2$), and metalation with $Zn(OAc)_2 \cdot 2H_2O$ followed by chromatography (silica, $CHCl_3$) afforded a purple solid (161 mg, 21%): mp onset 340° C.; $^1H$ NMR δ 1.85 (s, 6H), 2.64 (s, 3H), 2.71 (s, 6H), 3.76 (d, J=6.8 Hz, 2H), 5.27-5.37 (m, 2H), 6.29 (m, 1H), 7.29 (s, 2H), 7.55-7.58 (m, 6H), 8.11-8.16 (m, 6H), 8.79 (d, J=4.8 Hz, 2H), 8.92 (d, J=4.8 Hz, 2H), 8.96 (s, 4H); LDMS obsd 828.5, 845.5; FABMS obsd 828.3151, calcd 828.3170 ($C_{55}H_{48}N_4Zn$). $\lambda_{abs}$ 425, 485, 513, 551, 592 nm.

Zn(II)-5-(4-Allylphenyl)-10,20-di-p-tolyl-15-(2,4,6-triethylphenyl)porphyrin (Zn16). Following the procedure for Zn11, the condensation of 34-diol (derived from 34-$SnBu_2$; 483 mg, 0.625 mmol) and 28 (163 mg, 0.625 mmol) for 30 min, oxidation with DDQ, passage through a silica pad ($CH_2Cl_2$), metalation with $Zn(OAc)_2 \cdot 2H_2O$, and chromatography (silica, $CHCl_3$) afforded a purple solid (51 mg, 10%): mp onset 250° C.; $^1H$ NMR δ 0.74 (t, J=7.2 Hz, 6H), 1.54 (t, J=7.4 Hz, 3H), 2.09 (q, 4H), 2.72 (s, 6H), 3.00 (q, 2H), 3.76 (d, J=6.6 Hz, 2H), 5.27-5.38 (m, 2H), 6.26-6.35 (m, 1H), 7.35 (s, 2H), 7.54-7.59 (m, 6H), 8.12-8.17 (m, 6H), 8.80 (d, J=4.5 Hz, 2H), 8.92 (d, J=4.5 Hz, 2H), 8.97 (s, 4H); LDMS obsd 828.5; FABMS obsd 828.3151, calcd 828.3170 ($C_{55}H_{48}N_4Zn$); $\lambda_{abs}$ 425, 513, 551, 592 nm.

Zn(II)-5-(4-Allylphenyl)-10,20-dimethyl-15-p-tolylporphyrin (Zn17). Following the procedure for Zn11, the condensation of 35-diol (derived from 35-$SnBu_2$; 427 mg, 0.740 mmol) and 29 (175 mg, 0.741 mmol) for 30 min, oxidation with DDQ, passage through a silica pad ($CH_2Cl_2$), and metalation with $Zn(OAc)_2 \cdot 2H_2O$ followed by chromatography (silica, $CHCl_3$) afforded a purple solid (69 mg, 15%): mp onset 335° C.; $^1H$ NMR δ 2.73 (s, 3H), 3.77 (d, J=6.6 Hz, 2H), 4.67 (s, 6H), 5.29-5.40 (m, 2H), 6.25-6.39 (m, 1H), 7.56-7.60 (m, 4H), 8.07-8.14 (m, 4H), 8.98-9.00 (m, 4H), 9.56 (d, J=4.5 Hz, 4H); LDMS obsd 605.3; FABMS obsd 606.1798, calcd 606.1762 ($C_{38}H_{30}N_4Zn$); $\lambda_{abs}$ 425, 515, 554, 597 nm.

Zn(II)-5-(4-Allylphenyl)-15-mesityl-10,20-dimethylporphyrin (Zn18). Following the procedure for Zn11, the condensation of 35-diol (derived from 35-$SnBu_2$; 427 mg, 0.740 mmol) and 30 (196 mg, 0.740 mmol) for 30 min, oxidation with DDQ, passage through a silica pad ($CH_2Cl_2$), and metalation with $Zn(OAc)_2 \cdot 2H_2O$ followed by chromatography (silica, $CHCl_3$) afforded a purple solid (90 mg, 19%): mp onset 290° C.; $^1H$ NMR δ 1.83 (s, 6H), 2.66 (s, 3H), 3.77 (d, J=6.6 Hz, 2H), 4.66 (s, 6H), 5.29-5.40 (m, 2H), 6.25-6.39 (m, 1H), 7.30 (s, 2H), 7.58 (d, J=7.8 Hz, 2H), 8.11 (d, J=7.8 Hz, 2H), 8.82 (d, J=4.5 Hz, 2H), 8.95 (d, J=4.5 Hz, 2H), 9.53 (d, J=4.5 Hz, 4H); LDMS obsd 634.4; FABMS obsd 634.2120, calcd 634.2075 ($C_{40}H_{34}N_4Zn$); $\lambda_{abs}$ 424, 515, 553, 597 nm.

Zn(II)-5-(4-Allylphenyl)-10,20-dimethyl-15-(2,4,6-triethylphenyl)porphyrin (Zn19). Following the procedure for Zn11, the condensation of 35-diol (derived from 35-$SnBu_2$; 427 mg, 0.740 mmol) and 31 (227 mg, 0.740 mmol) for 25 min, oxidation with DDQ, passage through a silica pad ($CH_2Cl_2$), and metalation with $Zn(OAc)_2 \cdot 2H_2O$ followed by chromatography [silica, $CHCl_3$/hexanes (1:1)] afforded a purple solid (45 mg, 9%): mp onset 230° C.; $^1H$NMR δ 0.71 (t, J=7.5 Hz, 6H), 1.56 (t, J=7.5 Hz, 3H) 2.10 (q, 4H), 2.99 (q, 2H), 3.77 (d, J=6.6 Hz, 2H), 4.66 (s, 6H), 5.29-5.40 (m, 2H), 6.25-6.39 (m, 1H), 7.34 (s, 2H), 7.58 (d, J=7.8 Hz, 2H), 8.11 (d, J=7.8 Hz, 2H), 8.82 (d, J=4.5 Hz, 2H), 8.95 (d, J=4.5 Hz, 2H), 9.50 (d, J=4.5 Hz, 2H), 9.54 (d, J=4.5 Hz, 2H); LDMS obsd 676.4; FABMS obsd 676.2580, calcd 676.2544 ($C_{43}H_{40}N_4Zn$); $\lambda_{abs}$ 425, 515, 554, 597 nm.

1-Iodo-4-(1,1-dimethoxymethyl)benzene (20). A solution of 4-iodobenzaldehyde (10.0 g, 43.1 mmol) in MeOH (150 mL) was treated with $TiCl_4$ (80 μL, 430 μmol) under argon for 15 min. TEA (0.2 mL) was added. After 15 min, water and $Et_2O$ were added. The organic layer was collected, dried ($Na_2SO_4$), filtered, and concentrated to give a pale yellow oil (11.5 g, 96%): $^1H$ NMR δ 3.30 (s, 6H), 5.34 (s, 1H), 7.19 (d, J=8.4 Hz, 2H), 7.70 (d, J=8.4 Hz, 2H); $^{13}C$ NMR δ 52.4, 94.3, 102.1, 128.6, 137.1, 137.6.

1-(1,1-Dimethoxymethyl)-4-vinylbenzene (21). A sample of 20 (8.50 g, 30.6 mmol) was treated with vinylmagnesium bromide (33.6 mL, 33.6 mmol, 1.0 M solution in THF) followed by $Pd(PPh_3)_2Cl_2$ (220 mg, 1 mol %). The mixture was stirred at room temperature under argon for 2 h. Water and $Et_2O$ were added. The aqueous layer was washed with $Et_2O$. The organic layer was collected, dried ($Na_2SO_4$), filtered, and concentrated. Chromatography [silica, $Et_2O$/hexanes/TEA (25:75:1)] afforded a colorless oil (3.51 g, 64%): $^1H$ NMR δ 3.33 (s, 6H), 5.25 (d, J=10.0 Hz, 1H), 5.39 (s, 1H), 5.75 (d, J=16.8 Hz, 1H), 6.72 (dd, $J^1$=16.8 Hz, $J^2$=10.0 Hz, 1H), 7.41 (s, 4H); $^{13}C$ NMR δ 52.3, 102.6, 113.9, 125.9, 126.5, 126.8, 128.0, 136.3, 137.4, 137.5; FABMS obsd 178.0944, calcd 178.0994 ($C_{11}H_{14}O_2$).

4-Allylbenzaldehyde (23). Following a standard procedure,[38] a solution of 22 (2.36 g, 10.2 mmol) in $CH_2Cl_2$ (60 mL) was treated with TFA (12 mL) and water (0.3 mL). The solution was stirred for 18 h. Then aqueous NaHCO$_3$ (5%, 150 mL) was added. The organic phase was washed with aqueous NaHCO$_3$ and brine, then dried (Na$_2$SO$_4$) and concentrated. Chromatography (silica, CH$_2$Cl$_2$/hexanes, 1:2) afforded a colorless oil that partially solidified after standing at 0° C. for a few weeks (1.20 g, 81%): $^1$H NMR δ 3.47 (d, J=6.4 Hz 2H), 5.09-5.15 (m, 2H), 5.92-5.99 (m, 1H), 7.36 (d, J=8.4 Hz, 2H), 7.82 (d, J=8.0 Hz, 2H), 9.81 (s, 1H); $^{13}$C NMR 40.1, 116.7, 129.1, 129.8, 134.5, 135.9, 147.2, 191.7; FABMS obsd 146.0739, calcd 146.0732 (C$_{10}$H$_{10}$O).

5-Allyldipyrromethane (24). Following a standard procedure,[40,41] a solution of 3-butenal diethylacetal (4.00 g, 27.7 mmol) in pyrrole (194 mL, 2.77 mol) at room temperature under argon was treated with TFA (467 μL, 2.77 mmol) for 10 min. TEA (221 μL, 2.77 mmol) was added. The mixture was concentrated under high vacuum. The residue was chromatographed [silica, hexanes/ethyl acetate (4:1)] to afford a pale orange oil (1.85 g, 36%): $^1$H NMR δ 2.86 (t, J=8.0 Hz, 2H), 4.11 (t, J=8.0 Hz, 1H), 5.02-5.12 (m, 2H), 5.83 (m, 1H), 6.08 (s, 2H), 6.15 (m, 2H), 6.65 (m, 2H), 7.83 (br s, 2H); $^{13}$C NMR δ 37.3, 38.7, 105.6, 107.6, 116.3, 117.1, 132.8, 136.2; FABMS obsd 187.1230, calcd 187.1235 [(M+H)$^+$], (M=C$_{12}$H$_{14}$N$_2$).

5-(3-Butenyl)dipyrromethane (25). Following a standard procedure,[42] a solution of 4-pentenal (4.00 g, 47.6 mmol) in pyrrole (332 mL, 4.76 mol) at room temperature under argon was treated with InCl$_3$ (1.05 g, 4.76 mmol) for 1.5 h. Powdered NaOH (5.71 g, 143 mmol) was added. After stirring for 30 min, the mixture was suction-filtered. The filtrate was concentrated under high vacuum. The resulting residue was chromatographed [silica, hexanes/ethyl acetate (4:1)] to afford a pale yellow oil (7.48 g, 78%): $^1$H NMR δ 2.05 (m, 4H), 4.00 (m, 1H), 4.96-5.05 (m, 2H), 5.80 (m, 1H), 6.08 (s, 2H), 6.15 (m, 2H), 6.62 (m, 2H), 7.71 (br s, 2H); $^{13}$C NMR δ 31.3, 33.1, 36.5, 105.5, 107.6, 114.9, 117.1, 133.1, 138.0; FABMS obsd 200.1321, calcd 200.1313 (C$_{13}$H$_{16}$N$_2$).

5-(4-Vinylphenyl)dipyrromethane (27). Following the procedure for 25, the reaction of 21 (2.78 g, 15.6 mmol) in pyrrole (108 mL, 1.56 mol) and the standard workup including chromatography (silica, CH$_2$Cl$_2$ followed by silica, toluene) afforded a yellow solid (2.52 g, 65%): mp 75-78° C.; $^1$H NMR δ(CD$_2$Cl$_2$) 5.24 (d, J=10.0 Hz, 1H), 5.44 (s, 1H), 5.75 (d, J=16.8 Hz, 1H), 5.87-5.88 (m, 2H), 6.11-6.13 (m, 2H), 6.68-6.76 (m, 3H), 7.17 (d, J=8.0 Hz, 2H), 7.38 (d, J=8.0 Hz, 2H), 8.01 (brs, 2H); $^{13}$C NMR δ (CD$_2$Cl$_2$) 44.2, 107.5, 108.8, 114.1, 117.8, 126.9, 129.0, 133.0, 136.8, 136.9, 142.6; FABMS obsd 248.1311, calcd 248.1313; Anal. Calcd for C$_{17}$H$_{16}$N$_2$: C, 82.22; H, 6.49; N, 11.28; Found. C, 82.44; H, 6.45; N, 11.24.

5-(4-Allylphenyl)dipyrromethane (28). Following the procedure for 25, the reaction of 23 (1.75 g, 12.0 mmol) in pyrrole (83 mL, 1.2 mol) and the standard workup including chromatography (silica, toluene) followed by recrystallization from EtOH/H$_2$O (6:1) afforded an off-white solid (1.92 g, 61%): mp 60-62° C.; $^1$H NMR δ 3.37 (d, J=8.0 Hz, 2H), 5.06-5.11 (m, 2H), 5.46 (s, 1H), 5.93-5.99 (m, 3H), 6.15-6.17 (m, 2H), 6.69-6.70 (m, 2H), 7.15 (s, 4H), 7.91 (brs, 2H); $^{13}$C NMR δ 39.8, 43.6, 107.1, 108.4, 115.9, 117.1, 128.4, 128.8, 132.6, 137.3, 138.8, 139.8; FABMS obsd 262.1476, calcd 262.1470; Anal. Calcd for C$_{18}$H$_{18}$N$_2$: C, 82.41; H, 6.92; N, 10.68; Found. C, 82.44; H, 6.85; N, 10.44.

5-(2,4,6-Triethylphenyl)dipyrromethane (31). Following a standard procedure for mesitaldehyde,[42] a solution of 2,4,6-triethylbenzaldehyde (5.70 g, 30.0 mmol) in pyrrole (210 mL, 3.00 mol) was treated with MgBr$_2$ (2.76 g, 15.0 mmol) at room temperature for 1 h. Powdered NaOH (6.0 g, 15 mmol) was added. After stirring for 30 min, the mixture was suction-filtered. The filtrate was concentrated under high vacuum. Chromatography (silica, CHCl$_3$ followed by silica, toluene) of the residue afforded a brown oil (5.22 g, 57%): $^1$H NMR δ 0.93 (brs, 6H), 1.28 (t, J=8.0 Hz, 3H), 2.53 (brs, 4H), 2.64 (q, J=7.6 Hz, 2H), 5.96 (s, 1H), 6.07 (s, 2H), 6.19 (m, 2H), 6.66 (s, 2H), 6.97 (s, 2H), 7.95 (brs, 2H); $^{13}$C NMR δ 15.2, 27.0, 28.3, 37.3, 106.4, 108.3, 115.9, 127.3, 131.8, 133.1, 143.1; FABMS obsd 306.2103, calcd 306.2096 (C$_{21}$H$_{26}$N$_2$).

Dibutyl[5,10-dihydro-1,9-d]-p-toluoyl-5-p-tolyldipyrrinato]tin(IV) (32-SnBu$_2$). Following a general diacylation procedure,[39] a solution of 29 (5.00 g, 21.2 mmol) in toluene (125 mL) was treated with EtMgBr (100 mL, 100 mmol, 1.0 M in THF) followed by p-toluoyl chloride (7.0 mL, 53 mmol). After quenching and extractive workup, the crude material was dissolved in CH$_2$Cl$_2$ (200 mL). Samples of TEA (8.9 mL, 64 mmol) and Bu$_2$SnCl$_2$ (6.44 g, 21.2 mmol) were added. After 30 min, the solution was concentrated. Column chromatography (silica, CH$_2$Cl$_2$) followed by crystallization (MeOH) afforded a pale green solid (8.54 g, 57%): mp 124-126° C.; $^1$H NMR δ 0.69 (t, J=7.2 Hz, 3H), 0.74 (t, J=7.2 Hz, 3H), 1.09-1.14 (m, 2H), 1.19-1.25 (m, 2H), 1.30-1.34 (m, 2H), 1.41-1.45 (m, 2H), 1.47-1.52 (m, 2H), 1.66-1.70 (m, 2H), 2.31 (s, 3H), 2.44 (s, 6H), 5.56 (s, 1H), 6.19 (d, J=4.0 Hz, 2H), 7.08-7.11 (m, 6H), 7.29 (d, J=8.0 Hz, 4H), 7.82 (d, J=8.0 Hz, 4H); $^{13}$C NMR δ 13.55, 13.57, 21.0, 21.5, 23.9, 24.7, 25.9, 26.3, 27.16, 27.22, 45.2, 115.0, 123.7, 127.9, 129.0, 129.1, 129.3, 135.0, 135.7, 136.2, 141.3, 142.0, 151.7, 184.3; FABMS obsd 705.2503, calcd 705.2525 [(M+H)$^+$]; Anal. Calcd for C$_{40}$H$_{44}$N$_2$O$_2$Sn; C, 68.29; H, 6.30; N, 3.98; Found. C, 68.33; H, 6.35; N, 3.92.

Dibutyl[5,10-dihydro-5-mesityl-1,9-d]-p-toluoyldipyrrinato]tin(IV) (33-SnBu$_2$). Following the procedure for 32-SnBu$_2$, the reaction of 30 (2.00 g, 7.57 mmol) and p-toluoyl chloride (2.00 mL, 15.1 mmol) followed by tin complexation (TEA, 3.2 mL, 23 mmol; Bu$_2$SnCl$_2$, 2.30 g, 7.57 mmol), chromatography (silica, CH$_2$Cl$_2$), and precipitation (diethyl ether/MeOH) afforded a pale yellow solid (2.87 g, 52%): mp 151-153° C.; $^1$H NMR δ 0.71 (t, J=7.2 Hz, 3H), 0.78 (t, J=7.2 Hz, 3H), 1.11-1.21 (m, 2H), 1.21-1.36 (m, 4H), 1.43-1.55 (m, 4H), 1.70-1.78 (m, 5H), 2.32 (s, 3H), 2.43 (s, 6H), 2.51 (s, 3H), 5.81 (d, J=4.0 Hz, 2H), 5.93 (s, 1H), 6.81 (s, 1H), 6.98 (s, 1H), 7.04 (d, J=4.0 Hz, 2H), 7.29 (d, J=8.0 Hz, 4H), 7.81 (d, J=8.0 Hz, 4H); $^{13}$C NMR δ 13.6, 20.3, 20.7, 20.9, 21.6, 23.5, 24.9, 26.2, 26.4, 27.5, 40.0, 113.9, 123.8, 128.7, 129.0, 130.7, 135.1, 135.3, 136.0, 136.3, 136.4, 138.1, 141.9, 151.9, 183.9; FABMS obsd 733.2826, calcd 733.2816 [(M+H)$^+$]; Anal. calcd for C$_{42}$H$_{48}$N$_2$O$_2$Sn; C, 68.96; H, 6.61; N, 3.83; Found. C, 68.84; H, 6.61; N, 3.76.

Dibutyl[5,10-dihydro-5-(2,4,6-triethylphenyl)-1,9-d]-p-toluoyldipyrrinato]tin(IV) (34-SnBu$_2$). Following the procedure for 32-SnBu$_2$, the reaction of 31 (2.00 g, 6.52 mmol) and p-toluoyl chloride (2.16 mL, 16.3 mmol) followed by tin complexation (TEA, 2.7 mL, 20 mmol; Bu$_2$SnCl$_2$, 1.98 g, 6.52 mmol), chromatography (silica, CH$_2$Cl$_2$), and precipitation (diethyl ether/MeOH) afforded a pink solid (1.96 g, 39%): mp 136-138° C.; $^1$H NMR δ 0.71-0.79 (m, 9H), 1.18-1.30 (m, 12H), 1.47-1.56 (m, 4H), 1.74 (m, 2H), 2.08 (q, J=8.0 Hz, 2H), 2.43 (s, 6H), 2.66 (q, J=8.0 Hz, 2H), 2.81 (q, J=2H), 5.81 (d, J=4.0 Hz, 2H), 5.88 (s, 1H), 6.93 (s, 1H), 6.98 (s, 1H), 7.01 (d, J=4.0 Hz, 2H), 7.29 (d, J=8.0 Hz, 4H), 7.81 (d, J=8.0 Hz, 4H); $^{13}$C NMR δ 13.7, 13.8, 15.3, 16.7, 21.6, 23.5, 24.8, 25.3, 26.2, 26.5, 27.4, 27.5, 28.1, 28.5, 39.4, 114.7, 123.6, 125.9, 127.1, 129.01, 129.04, 135.2, 135.3, 135.4, 141.9, 142.1, 142.9, 143.9, 152.8, 183.9; FABMS obsd 775.3292, calcd 775.3286 [(M+H)$^+$]; Anal. calcd for $C_{45}H_{54}N_2O_2Sn$; C, 69.86; H, 7.04; N, 3.62; Found. C, 69.96; H, 7.00; N, 3.58.

Dibutyl[1,9-d]acetyl-5-(4-allylphenyl)-5,10-dihydrodipyrrinato]tin(IV) (35-SnBu$_2$). Following the procedure for 32-SnBu$_2$, the reaction of 28 (1.40 g, 5.34 mmol) and acetyl bromide (0.992 mL, 13.4 mmol) followed by tin complexation (TEA, 2.2 mL, 16 mmol; Bu$_2$SnCl$_2$, 1.62 g, 5.34 mmol), chromatography (silica, CH$_2$Cl$_2$), and precipitation (diethyl ether/MeOH) afforded a pale yellow solid (1.50 g, 57%): mp 54-56° C.; $^1$H NMR δ 0.70 (t, J=7.6 Hz, 3H), 0.75 (t, J=7.6 Hz, 3H), 1.05-1.57 (m, 12H), 2.41 (s, 6H), 3.31 (d, J=6.8 Hz, 2H), 5.02-5.07 (m, 2H), 5.48 (s, 1H), 5.88-5.95 (m, 1H), 6.10 (d, J=4.0 Hz, 2H), 7.02-7.07 (m, 6H); $^{13}$C NMR δ 13.49, 13.52, 23.2, 23.4, 24.2, 25.9, 26.3, 27.1, 39.7, 44.8, 114.2, 115.7, 120.8, 127.8, 128.0, 128.7, 136.6, 137.3, 138.2, 142.2, 150.7, 188.3; FABMS obsd 579.2036, calcd 579.2034 [(M+H)$^+$]; Anal. calcd for $C_{30}H_{38}N_2O_2Sn$; C, 62.41; H, 6.63; N, 4.85; Found. C, 62.46; H, 6.67; N, 4.86.

5,10,15-Tri-p-tolylporphyrin (37). Following the procedure for Zn11, the condensation of 32-diol (derived from 32, 1.42 g, 3.00 mmol) and 36 (440 mg, 3.01 mmol) for 20 min, oxidation with DDQ, addition of TEA (3 mL), and chromatography [silica, hexanes/CH$_2$Cl$_2$, (1:2)] afforded a purple solid (477 mg, 27%): $^1$H NMR δ −2.97 (s, 2H), 2.70-2.75 (br s, 9H), 7.56 (d, J=8.0 Hz, 2H), 7.60 (d, J=8.0 Hz, 4H), 8.11 (d, J=8.0 Hz, 2H), 8.14 (d, J=8.0 Hz, 4H), 8.89-8.95 (m, 4H), 9.05 (d, J=4.4 Hz, 2H), 9.33 (d, J=4.4 Hz, 2H), 10.20 (s, 1H); LDMS obsd 580.4; FABMS obsd 580.2635, calcd 580.2627 ($C_{41}H_{32}N_4$); $\lambda_{abs}$ 414, 509, 544, 585, 641 nm.

REFERENCES (1) For recent reviews, see: (a) Kwok, K. S.; Ellenbogen, J. C. *Materials Today* 2002, 5, 28-37. (b) Carroll, R. L.; Gorman, C. B. *Angew. Chem. Int. Ed.* 2002, 41, 4378-4400.

(2) Roth, K. M.; Dontha, N.; Dabke, R. B.; Gryko, D. T.; Clausen, C.; Lindsey, J. S.; Bocian, D. F.; Kuhr, W. G. *J. Vac. Sci. Technol. B* 2000, 18, 2359-2364.

(3) Li, Q.; Mathur, G.; Homsi, M.; Surthi, S.; Misra, V.; Malinovskii, V.; Schweikart, K.-H.; Yu, L.; Lindsey, J. S.; Liu, Z.; Dabke, R. B.; Yasseri, A.; Bocian, D. F.; Kuhr, W. G. *Appl. Phys. Lett.* 2002, 81, 1494-1496.

(4) Liu, Z.; Yasseri, A. A.; Lindsey, J. S.; Bocian, D. F. *Science* 2003, 302, 1543-1545.

(5) Roth, K. M.; Liu, Z.; Gryko, D. T.; Clausen, C.; Lindsey, J. S.; Bocian, D. F.; Kuhr, W. G. *Molecules as Components of Electronic Devices*; ACS Symposium Series 844; American Chemical Society: Washington, D.C., 2003, pp 51-61.

(6) Roth, K. M.; Yasseri, A. A.; Liu, Z.; Dabke, R. B.; Malinovskii, V.; Schweikart, K.-H.; Yu, L.; Tiznado, H.; Zaera, F.; Lindsey, J. S.; Kuhr, W. G.; Bocian, D. F. *J. Am. Chem. Soc.* 2003, 125, 505-517.

(7) (a) Song, J. H.; Sailor, M. J. *Comments Inorg. Chem.* 1999, 21, 69-84. (b) Buriak, J. M. *Chem. Commun.* 1999, 1051-1060. (c) Hamers, R. J.; Coulter, S. K.; Ellison, M. D.; Hovis, J. S.; Padowitz, D. F.; Schwartz, M. P.; Greenlief, C. M.; Russell, J. N., Jr. *Acc. Chem. Res.* 2000, 33, 617-624. (d) Buriak, J. M. *Chem. Rev.* 2002, 102, 1271-1308. (e) Bent, S. F. *Surf. Sci.* 2002, 500, 879-903. (f) Stewart, M. P.; Buriak, J. M. *Comments Inorg. Chem.* 2002, 23, 179-203.

(8) Cleland, G.; Horrocks, B. R.; Houlton, A. *J. Chem. Soc. Faraday Trans.* 1995, 91, 4001-4003.

(9) Kim, N. Y.; Laibinis, P. E. *J. Am. Chem. Soc.* 1997, 119, 2297-2298.

(10) Zhu, X.-Y.; Boiadjiev, V.; Mulder, J. A.; Hsung, R. P.; Major, R. C. *Langmuir* 2000, 16, 6766-6772.

(11) Boukherroub, R.; Morin, S.; Sharpe, P.; Wayner, D. D. M.; Allongue, P. *Langmuir* 2000, 16, 7429-7434.

(12) Balakumar, A.; Lysenko, A. B.; Carcel, C.; Malinovskii, V. L.; Gryko, D. T.; Schweikart, K.-H.; Loewe, R. S.; Yasseri, A. A.; Liu, Z.; Bocian, D. F.; Lindsey, J. S. *J. Org. Chem.* 2004, 69, 1435-1443.

(13) International Technology Roadmap for Semiconductors, 2003 Edition, http://public.itrs.net.

(14) Linford, M. R.; Chidsey, C. E. D. *J. Am. Chem. Soc.* 1993, 115, 12631-12632.

(15) Linford, M. R.; Fenter, P.; Eisenberger, P. M.; Chidsey, C. E. D. *J. Am. Chem. Soc.* 1995, 117, 3145-3155.

(16) Bansal, A.; Li, X.; Lauermann, I.; Lewis, N. S.; Yi, S. I.; Weinberg, W. H. *J. Am. Chem. Soc.* 1996, 118, 7225-7226.

(17) Allongue, P.; de Villeneuve, C. H.; Pinson, J.; Ozanam, F.; Chazalviel, J. N.; Wallart, X. *Electrochim. Acta* 1998, 43, 2791-2798.

(18) Gurtner, C.; Wun, A. W.; Sailor, M. J. *Angew. Chem. Int. Ed.* 1999, 38, 1966-1968.

(19) Fellah, S.; Teyssot, A.; Ozanam, F.; Chazalviel, J.-N.; Vigneron, J.; Etcheberry, A. *Langmuir* 2002, 18, 5851-5860.

(20) Bateman, J. E.; Eagling, R. D.; Worrall, D. R.; Horrocks, B. R.; Houlton, A. *Angew. Chem. Int. Ed.* 1998, 37, 2683-2685.

(21) Boukherroub, R.; Morin, S.; Wayner, D. D. M.; Bensebaa, F.; Sproule, G. I.; Baribeau, J.-M.; Lockwood, D. J. *Chem. Mater.* 2001, 13, 2002-2011.

(22) Wagner, P.; Nock, S.; Spudich, J. A.; Volkmuth, W. D.; Chu, S.; Cicero, R. L.; Wade, C. P.; Linford, M. R.; Chidsey, C. E. D. *J. Struct. Biol.* 1997, 119, 189-201.

(23) Boukherroub, R.; Wayner, D. D. M. *J. Am. Chem. Soc.* 1999, 121, 11513-11515.

(24) Barrelet, C. J.; Robinson, D. B.; Cheng, J.; Hunt, T. P.; Quate, C. F.; Chidsey, C. E. D. *Langmuir* 2001, 17, 3460-3465.

(25) Zazzera, L. A.; Evans, J. F.; Deruelle, M.; Tirrell, M.; Kessel, C. R.; Mckeown, P. *J. Electrochem. Soc.* 1997, 144, 2184-2189.

(26) (a) Buriak, J. M.; Allen, M. J. *J. Am. Chem. Soc.* 1998, 120, 1339-1340. (b) Holland, J. M.; Stewart, M. P.; Allen, M. J.; Buriak, J. M. *J. Solid State Chem.* 1999, 147, 251-258. (c) Buriak, J. M.; Stewart, M. P.; Geders, T. W.; Allen, M. J.; Choi, H. C.; Smith, J.; Raftery, D.; Canham, L. T. *J. Am. Chem. Soc.* 1999, 121, 11491-11502.

(27) Cerofolini, G. F.; Galati, C.; Reina, S.; Renna, L. *Semicond. Sci. Technol.* 2003, 18, 423-429.

(28) Stewart, M. P.; Robins, E. G.; Geders, T. W.; Allen, M. J.; Choi, H. C.; Buriak, J. M. *Phys. Stat. Sol.* 2000, 182, 109-115.

(29) Wagner, R. W.; Ciringh, Y.; Clausen, C.; Lindsey, J. S. *Chem. Mater.* 1999, 11, 2974-2983.

(30) Loewe, R. S.; Ambroise, A.; Muthukumaran, K.; Padmaja, K.; Lysenko, A. B.; Mathur, G.; Li, Q.; Bocian, D. F.; Misra, V.; Lindsey, J. S. *J. Org. Chem.* 2004, 69, 1453-1460.

(31) Wagner, R. W.; Johnson, T. E.; Lindsey, J. S. *J. Am. Chem. Soc.* 1996, 118, 11166-11180.

(32) Wagner, R. W.; Johnson, T. E.; Li, F.; Lindsey, J. S. *J. Org. Chem.* 1995, 60, 5266-5273.

(33) Tamao, K.; Sumitani, K.; Kumada, M. *J. Am. Chem. Soc.* 1972, 94, 4374-4376.

(34) Lindsey, J. S.; Prathapan, S.; Johnson, T. E.; Wagner, R. W. *Tetrahedron* 1994, 50, 8941-8968.

(35) Wagner, R. W.; Li, F.; Du, H.; Lindsey, J. S. *Org. Process Res. Dev.* 1999, 3, 28-37.
(36) Lindsey, J. S.; Wagner, R. W. *J. Org. Chem.* 1989, 54, 828-836.
(37) Gryko, D. T.; Clausen, C.; Roth, K. M.; Dontha, N.; Bocian, D. F.; Kuhr, W. G.; Lindsey, J. S. *J. Org. Chem.* 2000, 65, 7345-7355.
(38) Lindsey, J. S.; Brown, P. A.; Siesel, D. A. *Tetrahedron* 1989, 45, 4845-4866.
(39) Rao, P. D.; Dhanalekshmi, S.; Littler, B. J.; Lindsey, J. S. *J. Org. Chem.* 2000, 65, 7323-7344.
(40) Lee, C.-H.; Lindsey, J. S. *Tetrahedron* 1994, 50, 11427-11440.
(41) Littler, B. J.; Miller, M. A.; Hung, C.-H.; Wagner, R. W.; O'Shea, D. F.; Boyle, P. D.; Lindsey, J. S. *J. Org. Chem.* 1999, 64, 1391-1396.
(42) Laha, J. K.; Dhanalekshmi, S.; Taniguchi, M.; Ambroise, A.; Lindsey, J. S. *Org. Process Res. Dev.* 2003, 7, 799-812.
(43) Wilson, G. S.; Anderson, H. L. *Synlett* 1996, 1039-1040.
(44) Loewe, R. S.; Tomizaki, K.-Y.; Youngblood, W. J.; Bo, Z.; Lindsey, J. S. *J. Mater. Chem.* 2002, 12, 3438-3451.
(45) Tamara, S.-I.; Yu, L.; Youngblood, W. J.; Muthukumaran, K.; Taniguchi, M.; Lindsey, J. S. *J. Org. Chem.* 2004, 69, 765-777.
(46) Geier, G. R., III; Callinan, J. B.; Rao, P. D.; Lindsey, J. S. *J. Porphyrins Phthalocyanines* 2001, 5, 810-823.
(47) (a) Fenyo, D.; Chait, B. T.; Johnson, T. E.; Lindsey, J. S. *J. Porphyrins Phthalocyanines* 1997, 1, 93-99. (b) Srinivasan, N.; Haney, C. A.; Lindsey, J. S.; Zhang, W.; Chait, B. T. *J. Porphyrins Phthalocyanines* 1999, 3, 283-291.
(48) Gryko, D.; Lindsey, J. S. *J. Org. Chem.* 2000, 65, 2249-2252.
(49) Wang, Q. M.; Bruce, D. W. *Synlett* 1995, 1267-1268.
(50) (a) Shultz, D. A.; Gwaltney, K. P.; Lee, H. *J. Org. Chem.* 1998, 63, 769-774. (b) Shanmugathasan, S.; Johnson, C. K.; Edwards, C.; Matthews, E. K.; Dolphin, D.; Boyle, R. W. *J. Porphyrins Phthalocyanines* 2000, 4, 228-232.
(51) Stille, J. K. *Angew. Chem. Int. Ed. Engl.* 1986, 25, 508-524.
(52) Clausen, C.; Gryko, D. T.; Yasseri, A. A.; Diers, J. R.; Bocian, D. F.; Kuhr, W. G.; Lindsey, J. S. *J. Org. Chem.* 2000, 65, 7371-7378.
(53) Lee, C.-H.; Li, F.; Iwamoto, K.; Dadok, J.; Bothner-By, A. A.; Lindsey, J. S. *Tetrahedron* 1995, 51, 11645-11672.
(54) Latos-Grazynski, L. In *The Porphyrin Handbook*; Kadish, K. M., Smith, K. M., Guilard, R., Eds.; Academic Press: San Diego, Calif., 2000; Vol. 2, pp 361-416.
(55) Barbero, M.; Cadamuro, S.; Degani, I.; Dughera, S.; Fochi, R.; Gatti, A.; Prandi, C. *Gazz. Chim. Ital.* 1990, 120, 619-627.
(56) (a) Perlovich, G. L.; Golubchikov, O. A.; Klueva, M. E. *J. Porphyrins Phthalocyanines* 2000, 4, 699-706. (b) Semyannikov, P. P.; Basova, T. V.; Grankin, V. M.; Igumenov, I. K. *J. Porphyrins Phthalocyanines* 2000, 4, 271-277. (c) Torres, L. A.; Campos, M.; Enriquez, E.; Patino, R. *J. Chem. Thermodynamics* 2002, 34, 293-302.

The foregoing is illustrative of the present invention, and is not to be construed as limiting thereof. The invention is defined by the following claims, with equivalents of the claims to be included therein.

That which is claimed is:

1. A dipyrromethane compound having a surface attachment group coupled thereto at the 5 position, said surface attachment group having the formula:

wherein:
R is —CHCH$_2$ or —CCH;
Ar is an aromatic group;
m is 0 to 4;
n is 0 to 6; and
p is 0 to 3;
subject to the proviso that n is at least 1 or m is at least 2, and p is at least 1.

2. The dipyrromethane compound of claim 1 wherein R is —CCH.
3. The dipyrromethane compound of claim 1 wherein R is —CHCH$_2$.
4. The dipyrromethane compound of claim 1 wherein n is at least 1.
5. The dipyrromethane compound of claim 1 wherein m is at least 2.
6. The dipyrromethane compound of claim 1 wherein Ar is a phenyl group.
7. The dipyrromethane compound of claim 1 wherein:
p is 1; and
m and n together total from 1 to 5.
8. The dipyrromethane compound of claim 1 wherein:
R is —CHCH$_2$;
m is 0, 1 or 2;
n is 1 or 2; and
p is 1 or 2.
9. The dipyrromethane compound of claim 8 wherein p is 1.
10. The dipyrromethane compound of claim 8 wherein Ar is a phenyl group.
11. The dipyrromethane compound of claim 1, wherein said dipyrromethane is a 1,9-diacyldipyrromethane.
12. A method of making a dipyrromethane compound having a surface attachment group coupled thereto at the 5 position, said surface attachment group having the formula:

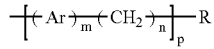

wherein:
R is CHCH$_2$ or CCH;
Ar is an aromatic group;
m is 0 to 4;
n is 0 to 6; and
p is 0 to 3; said method comprising:
Reacting a precursor compound of the formula:

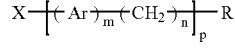

where X is an aldehyde or acetal group;
with a pyrrole to produce said dipyrromethane compound having said surface attachment group substituted therein at the 5 position.

13. A method of making a 1,9-diacyldipyrromethane metal complex, comprising:
(a) acylating a dipyrromethane compound having a surface attachment group coupled thereto at the 5 position, said surface attachment group having the formula:

wherein:
R is CHCH$_2$ or CCH;
Ar is an aromatic group;
m is 0 to 4;
n is 0 to 6; and
p is 0 to 3;

to form a mixed reaction product comprising a 1,9-diacyldipyrromethane;

(b) combining said mixed reaction product with a compound of the formula R'$_2$MX$_2$ in the presence of a base, where R' is alkyl or aryl, M is Sn, Si, Ge, or Pb, and X is halo, OAc, acac or OTf, to form a metal complex of the formula DMR'$_2$ in said mixed reaction product, wherein DH$_2$ is a 1,9-diacyldipyrromethane; and then (c) separating said metal complex from said mixed reaction product.

* * * * *